US012790368B2

(12) United States Patent
Birnbaum et al.

(10) Patent No.: US 12,790,368 B2
(45) Date of Patent: Nov. 10, 2026

(54) PEPTIDES CAPABLE OF ALTERING NK CELL ACTIVITY

(71) Applicants: Massachusetts Institute of Technology, Cambridge, MA (US); Deutsches Rheuma-Forschungszentrum Berlin, ein Leibniz-Institut, Berlin (DE); Charité—Universitätsmedizin Berlin, Berlin (DE)

(72) Inventors: Michael Birnbaum, Arlington, MA (US); Brooke Huisman, Clarkston, MI (US); Chiara Romagnani, Berlin (DE); Timo Rückert, Berlin (DE)

(73) Assignees: Massachusetts Institute of Technology, Cambridge, MA (US); Deutsches Rheuma-Forschungszentrum Berlin, ein Leibniz-Institut, Berlin (DE); Charité—Universitätsmedizin Berlin, Berlin (DE)

( * ) Notice: Subject to any disclaimer, the term of this patent is extended or adjusted under 35 U.S.C. 154(b) by 600 days.

(21) Appl. No.: 18/331,004

(22) Filed: Jun. 7, 2023

(65) Prior Publication Data

US 2024/0092835 A1 Mar. 21, 2024

Related U.S. Application Data

(60) Provisional application No. 63/350,844, filed on Jun. 9, 2022, provisional application No. 63/349,959, filed on Jun. 7, 2022.

(51) Int. Cl.

| | |
|---|---|
| ***C07K 7/06*** | (2006.01) |
| ***A61K 38/00*** | (2006.01) |
| ***A61P 37/04*** | (2006.01) |

(52) U.S. Cl.

CPC ................ *C07K 7/06* (2013.01); *A61P 37/04* (2018.01); *A61K 38/00* (2013.01)

(58) Field of Classification Search

None

See application file for complete search history.

(56) References Cited

U.S. PATENT DOCUMENTS

| | | | |
|---|---|---|---|
| 10,864,245 B2 | 12/2020 | Romagnani et al. | |
| 2009/0061459 A1 | 3/2009 | Polakiewicz et al. | |
| 2009/0130691 A1 | 5/2009 | Seidah et al. | |
| 2010/0151495 A9 | 6/2010 | Polakiewicz et al. | |
| 2020/0171135 A1 | 6/2020 | Lanier et al. | |
| 2021/0104294 A1 | 4/2021 | Hacohen et al. | |
| 2021/0382068 A1* | 12/2021 | Keskin | A61K 39/0011 |

FOREIGN PATENT DOCUMENTS

WO WO 2023/137156 A2 7/2023

OTHER PUBLICATIONS

Invitation to Pay Additional Fees for Application No. PCT/US2023/068073, mailed Sep. 22, 2023.

International Search Report and Written Opinion for Application No. PCT/US2023/068073, mailed Dec. 14, 2023.

International Preliminary Report on Patentability for Application No. PCT/US2023/068073, mailed Dec. 19, 2014.

Huisman et al., An unbiased characterization of the HLA-E and CD94/NKG2x peptide repertoire reveals peptide ligands that skew NK cell activation. BioRxiv. Aug. 5, 2022. 36 pages. Retrieved from the internet: URL: https://www.biorxiv.org/content/biorxiv/early/2022/08/05/2022.08.03.502719.full.pdf>.

Partial Supplementary European Search Report, mailed May 20, 2026, in connection with Application No. EP 23820618.9.

Extended European Search Report, mailed Aug. 10, 2026, in connection with Application No. EP 23820618.9.

Huisman et al., High-throughput characterization of HLA-E-presented CD94/NKG2x ligands reveals peptides which modulate NK cell activation. Nature Communications. Aug. 9, 2023;14(1):4809.

Lauterbach et al., HLA-E regulates NKG2C+ natural killer cell function through presentation of a restricted peptide repertoire. Human Immunology. Aug. 1, 2015;76(8):578-86.

Lind, K. Peptide Repertoire Changes Caused by Defects in Antigen Processing. 2013. Doctoral dissertation, UC Berkeley. 149 pages.

Llano et al., HLA-E-bound peptides influence recognition by inhibitory and triggering CD94/NKG2 receptors: preferential response to an HLA-G-derived nonamer. European Journal of Immunology. Sep. 1998;28(9):2854-63.

* cited by examiner

*Primary Examiner* — Sudhakar Katakam
*Assistant Examiner* — Zachary J Miknis
(74) *Attorney, Agent, or Firm* — Wolf, Greenfield & Sacks, P.C.

(57) ABSTRACT

Peptides capable of binding to HLA-E and affecting immune cell activity are provided. Such peptides can selectively activate NKG2C+ immune cells such as natural killer (NK) cells and/or can inhibit NKG2A+ cells to decrease or suppress immune cell responses. Methods of use of the peptides are also disclosed, for instance, for treating or inhibiting the development or progression of a multitude of illnesses and conditions, including autoimmune disease, infectious disease such as viral or bacterial infection, and proliferative disorders such as cancer.

16 Claims, 3 Drawing Sheets

Specification includes a Sequence Listing.

PEPTIDES CAPABLE OF ALTERING NK CELL ACTIVITY

RELATED APPLICATIONS

This application claims the benefit of priority under 35 U.S.C. § 119 of U.S. provisional application 63/349,959 filed Jun. 7, 2022, and of U.S. provisional application 63/350,844 filed Jun. 9, 2022, the entire contents of each of which are incorporated herein by reference.

FEDERALLY SPONSORED RESEARCH

This invention was made with government support under AI110495 awarded by the National Institutes of Health. The government has certain rights in the invention.

REFERENCE TO AN ELECTRONIC SEQUENCE LISTING

The contents of the electronic sequence listing (M065670523US02-SEQ-HCL.xml; Size: 17,470 bytes; and Date of Creation: Jun. 7, 2023) is herein incorporated by reference in its entirety.

BACKGROUND OF INVENTION

Natural killer (NK) cells are cytotoxic immune cells, which are important to innate immunity, are believed to bridge innate and adaptive immune responses. NK cells modulate their activity through cell-surface receptors such as CD94/NKG2A (NKG2A) and CD94/NKG2C (NKG2C). NKG2A and NKG2C bind to the non-classical MHC-Ib HLA-E protein:peptide complexes. In their classical role, NK cells bind HLA-E in complex with a constrained set of peptides (largely resembling VMAPRTLXL (SEQ ID NO: 16), where X is I, L, F, or V), derived from signal peptides of MHC class Ia molecules. NKG2A binding of HLA-E inhibits NK cells function, while NKG2C binding activates NK cells. NKG2A typically possess higher peptide binding affinity than the receptor NKG2C. Expression of NKG2A and NKG2C are exclusive to separate subsets of NK cells, with co-expression occurring in ~1-2% of NK cells.

Anti-NKG2A monoclonal antibodies are known to promote anti-tumor immunity, while NKG2C+NK cells are associated with diminished rates of leukemia and colorectal cancers, further highlighting the benefit NK cell modulation in disease states. Identification of HLA-E and peptide combinations capable of selective NKG2A or NKG2C receptor binding has been challenging due to the lack of HLA-E and NK cell receptor characterization. Similarities between NKG2A and NKG2C, when paired with the higher affinity of HLA-E peptide complexes to the inhibitory NKG2A receptor, make it challenging to identify or generate peptides capable of selectively activating NK cells through NKG2C.

SUMMARY OF INVENTION

In some aspects, a peptide including $X_1X_2PX_3RSLX_4X_5$ (SEQ ID NO. 1) are contemplated herein. In some embodiments, each x is an amino acid, wherein P is proline, R is Arginine, S is serine, L is Leucine, $X_1$ is Threonine or Valine, $X_2$ is Glycine or Asparagine, $X_3$ is Tryptophan or Glycine, $X_4$ is Tryptophan or Phenylalanine, and $X_5$ is Leucine or Isoleucine, and wherein the peptide is 9 to 25 amino acids in length.

In an embodiment, the peptide comprises TGPWRSLWI (SEQ ID NO. 2).

In an embodiment, the peptide consists essentially of TGPWRSLWI (SEQ ID NO. 2.

In an embodiment, the peptide consists of TGPWRSLWI (SEQ ID NO. 2.

In an embodiment, the peptide comprises VNPGRSLFL (SEQ ID NO. 3).

In an embodiment, the peptide consists essentially of VNPGRSLFL (SEQ ID NO. 3).

In an embodiment, the peptide consists of VNPGRSLFL (SEQ ID NO. 3).

In some aspects, a peptide including $X_1X_6PX_7RX_8X_9FL$ (SEQ ID NO:4) are contemplated herein. In some embodiments, each X is an amino acid, wherein P is proline, R is Arginine, F is Phenylalanine, L is Leucine, $X_1$ is Threonine or Valine, $X_6$ is Alanine or Asparagine, $X_7$ is Alanine or Glycine, $X_8$ is Serine or Threonine, and $X_9$ is Leucine or Methionine, and wherein the peptide is 9 to 25 amino acids in length.

In an embodiment, the peptide comprises TAPARTMFL (SEQ ID NO. 5).

In an embodiment, the peptide consists of TAPARTMFL (SEQ ID NO. 5).

In an embodiment, the peptide consists essentially of TAPARTMFL (SEQ ID NO. 5).

In an embodiment, the peptide comprises VNPGRSLFL (SEQ ID NO. 3).

In an embodiment, the peptide consists essentially of VNPGRSLFL (SEQ ID NO. 3).

In an embodiment, the peptide consists of VNPGRSLFL (SEQ ID NO. 3).

In an embodiment, the peptide has 9-20 amino acids in length.

In an embodiment, the peptide has 9-10 amino acids in length.

In an embodiment, the peptide is linear.

In an embodiment, the peptide is PEGylated.

In some aspects, a composition comprising a HLA-E binding peptide are described herein. In some embodiments, the peptide comprises, consists essentially of or consists of a sequence having at least 80% sequence identity to a sequence selected from TAPARTMFL (SEQ ID NO. 5), VNPGRSLFL (SEQ ID NO. 3), TGPWRSLWI (SEQ ID NO. 2), NMPARTVLF (SEQ ID NO. 6), QMPSRSLLF (SEQ ID NO. 7), TLPKRGLFL (SEQ ID NO. 8), ILTDRSLWL (SEQ ID NO. 9), FLPNRSLLF (SEQ ID NO. 10), TLPERTLYL (SEQ ID NO. 11), VMPGRTLCF (SEQ ID NO. 12), RMPPRSVLL (SEQ ID NO. 13), VMPPRTLLL (SEQ ID NO. 14), and VLPHRTQFL (SEQ ID NO. 15), and wherein the peptide is 9 to 25 amino acids in length, and a pharmaceutically acceptable carrier.

In some embodiments, the pharmaceutically acceptable carrier is a particle.

In some embodiments, the particle is a nanoparticle.

In some aspects, a method for treating a disease in a subject comprising administering to the subject a NKG2C+ cell activating peptide are contemplated herein. In some embodiments, wherein the NKG2C+ cell activating peptide comprises, consists essentially of or consists of a sequence having at least 80% sequence identity to a sequence selected from TAPARTMFL (SEQ ID NO. 5), VNPGRSLFL (SEQ ID NO. 3), TGPWRSLWI (SEQ ID NO. 2), QMPSRSLLF (SEQ ID NO. 7), TLPKRGLFL (SEQ ID NO. 8), ILTDRSLWL (SEQ ID NO. 9), and FLPNRSLLF (SEQ ID NO. 10).

In some embodiments, the disease is a viral infection.

In some embodiments, the viral infection is *Borrelia burgdorferi*, hepatitis virus, herpes virus, cytomegalovirus (CMV), Epstein bar virus (EBV), or human immunodeficiency virus (HIV).

In some embodiments, the disease is cancer.

In some aspects, a method for treating a disease in a subject comprising administering to the subject a NKG2A+ cell inhibitory peptide. In some embodiments, the NKG2A+ cell inhibitory peptide comprises a sequence having at least 80% sequence identity to NMPARTVLF (SEQ ID NO. 6).

In some embodiments, the disease is an autoimmune disease.

In some embodiments, the autoimmune disease is multiple sclerosis, systemic lupus erythematosus, inflammatory bowel disease, rheumatoid arthritis, Graves' disease, autoimmune thyroiditis, autoimmune myositis, discoid lupus erythematosus, Crohns disease, Sjogren's syndrome, Reiter's syndrome, Rheumatoid arthritis, myasthenia gravis, Kawasaki's disease, Celiac disease, Goodpasture's syndrome, or aplastic anemia.

BRIEF DESCRIPTION OF DRAWINGS

FIG. 1A: shows the effects of peptides on NKG2A+/NKG2C− inhibition by observing a reduction in CD107a+ NK cells.

FIG. 2A: shows the effects of the peptides NKG2A−/NKG2C+ cell activation by observing an increase CD107a+NK cells. FIG. 2B: shows the effects of the peptides NKG2A−/NKG2C+ cell activation by observing an increase TNF+NK cells. FIG. 2C: shows the effects of the peptides NKG2A−/NKG2C+ cell activation by observing an increase IFNG+NK cells. FIG. 2D: shows the effects of the peptides NKG2A−/NKG2C+ cell activation by observing an increase CCL3+NK cells.

FIG. 4A shows affinity measurements of peptide-HLA-E to CD94/NKG2A normalized to a fitted $R_{max}$. FIG. 4B shows affinity measurements of peptide-HLA-E to CD94/NKG2A normalized to theoretical $R_{max}$. FIG. 4C shows affinity measurements of peptide-HLA-E to CD94/NKG2C normalized to a fitted $R_{max}$. FIG. 4D shows affinity measurements of peptide-HLA-E to CD94/NKG2C normalized to theoretical $R_{max}$.

DETAILED DESCRIPTION OF INVENTION

Figure 1A:
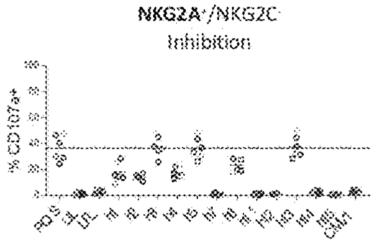
FIGS. 1A-IL show effects of the peptides on NKG2A+/NKG2C− and NKG2A−/NKG2C+ NK cells, when incubated with peptide and a target cell line (K562) expressing HLA-E. Human (h) peptides and CMV peptides are compared with positive control (VMAPRTLIL (LIL) (SEQ ID NO: 19) and VMAPRTLFL (LFL) (SEQ ID NO: 18)) and negative control PQS peptides for inhibition of NKG2A+/NKG2C− cells and activation of NKG2A−/NKG2C+ cells. Double negative NKG2A−/NKG2C− cells are included as a control.
Figure 1E:
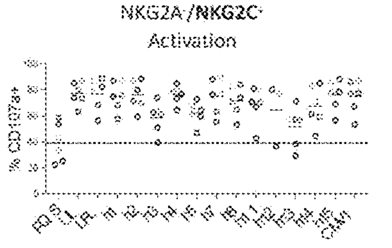
FIG. 1E: shows the effects of peptides on NKG2A−/NKG2C+ activation by observing a reduction in CD107a+ NK cells.
Figure 1I:
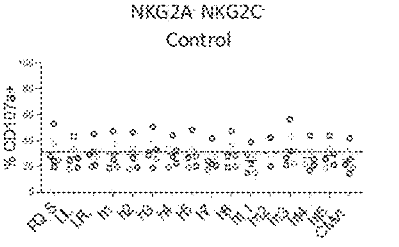
FIG. 1I: shows the effects of peptides on NKG2A−/NKG2C− control cells by observing no change in CD107a+ NK cells.
Figure 1B:
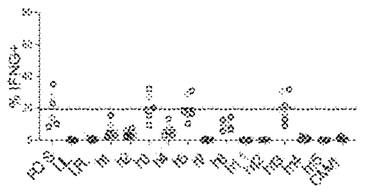
FIG. 1B: shows the effects of peptides on NKG2A+/NKG2C− inhibition by observing a reduction in IFNG+ NK cells.
Figure 1F:
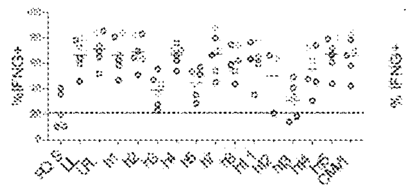
FIG. 1F: shows the effects of peptides on NKG2A−/NKG2C+ activation by observing an increase in IFNG+NK cells.
Figure 1J:
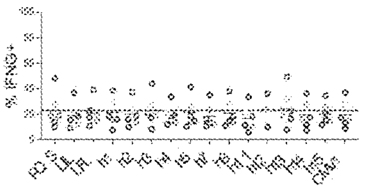
FIG. 1J: shows the effects of peptides on NKG2A−/NKG2C− control cells by observing no change in IFNG+NK cells.
Figure 1C:
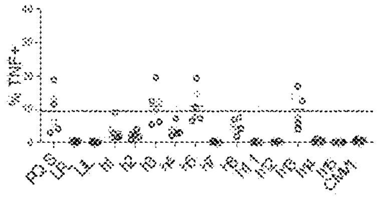
FIG. 1C: shows the effects of peptides on NKG2A+/NKG2C− inhibition by observing a reduction in TNF+ NK cells.
Figure 1G:
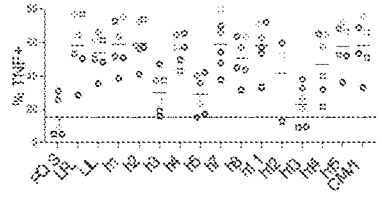
FIG. 1G: shows the effects of peptides on NKG2A−/NKG2C+ activation by observing an increase in TNF+NK cells.
Figure 1K:
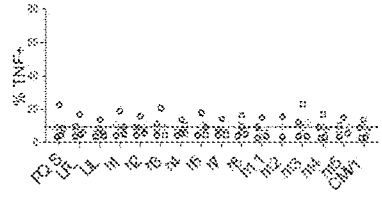
FIG. 1K: shows the effects of peptides on NKG2A−/NKG2C− control cells by observing no change in TNF+NK cells.
Figure 1D:
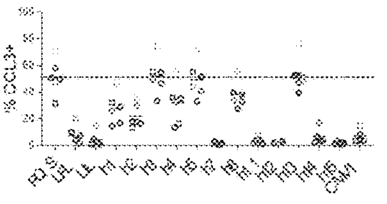
FIG. 1D: shows the effects of peptides on NKG2A+/NKG2C− inhibition by observing an increase in CCL3+NK cells.
Figure 1H:
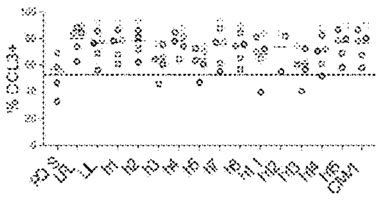
FIG. 1H: shows the effects of peptides on NKG2A−/NKG2C+ activation by observing an increase in CCL3+NK cells.
Figure 1L:
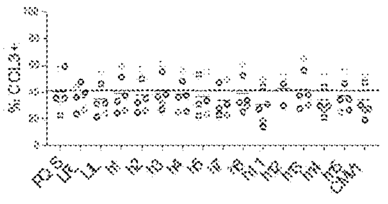
FIG. 1L: shows the effects of peptides on NKG2A−/NKG2C− control cells by observing no change in CCL3+NK cells.
Figure 2A:
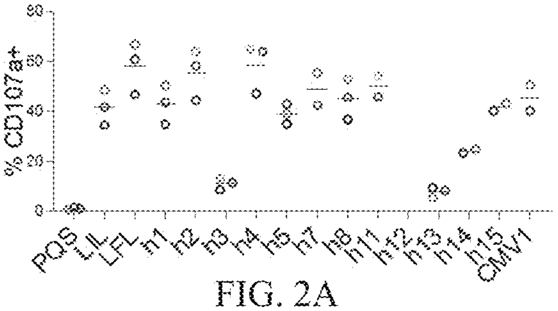
FIGS. 2A-2D shows greater granularity of the activating response of the peptides on NKG2A−/NKG2C+ cells, when incubated with peptide and a target cell line (RMA-S) expressing HLA-E.
Figure 2C:
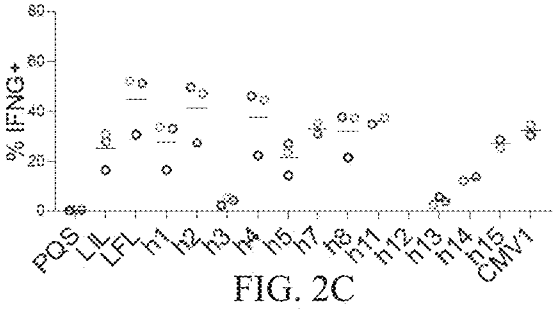
Figure 2B:
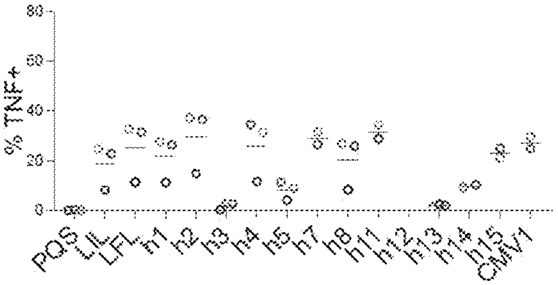
Figure 2D:
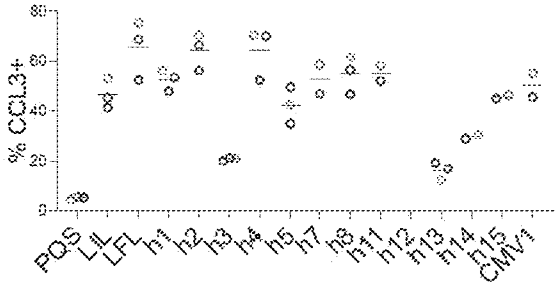

The present invention provides new insights into the role of peptides capable of binding to HLA-E and affecting immune cell activity. Such peptides can selectively activate NKG2C+ immune cells such as natural killer (NK) cells and/or can inhibit NKG2A+ cells to decrease or suppress immune cell responses. The result is a wide range of new therapeutic regimens for treating or inhibiting the development or progression of a multitude of illnesses and conditions, including autoimmune disease, infectious disease such as viral or bacterial infection, and proliferative disorders such as cancer.

Modulation of NK cell function and activity is of interest for therapeutic applications. Immune cells such as NK cells and T cells, have cell surface receptors that recognize cell surface peptide-HLA complexes on other cells. When the receptors are triggered, an intracellular signal is generated, in some instances leading to cell activation and in others leading to cell inhibition. Through this receptor activation these immune cells can regulate aspects of the immune response. For instance, activation of immune cells having HLA-E receptors can play a role in the innate immune system, likely acting to bridge innate and adaptive immune responses. One way in which NK cells modulate their activity is through receptors CD94/NKG2A (NKG2A) and CD94/NKG2C (NKG2C).

Both NKG2A and NKG2C bind to the highly-conserved class Ib MHC HLA-E complexed with a peptide. NKG2A is an inhibitory receptor and when activated triggers an intracellular signal that leads to inhibition of cellular activity. NKG2C is an activating receptor and when activated triggers an intracellular signal that leads to activation of the cells. NKG2A typically has a higher affinity for HLA-E than the activating receptor NKG2C. Expression of NKG2A and NKG2C are generally observed on separate subsets of NK cells, with co-expression occurring on only ~1-2% of NK cells though with a large degree of variability.

In their classical role, NK cells bind HLA-E in complex with a constrained set of peptides (largely resembling VMAPRTLXL (SEQ ID NO. 16), where X is I, L, F, or V), derived from signal peptides of class Ia MHC molecules. Recognition of HLA-E in complex with these peptides serves as a mechanism to assess 'missing self' signals. If these peptide-HLA-E complexes are downregulated, NK cell activity increases because of the loss of inhibition through the higher affinity, inhibitory NKG2A. Activating NKG2C+ subsets of NK cells may also be expanded in response to infections. Capitalizing on this activity can have important clinical implications. Synthetic peptides which can capitalize on this process have been developed.

The peptides disclosed herein bind to a human leukocyte antigen E (HLA-E). HLA-E is a major histocompatibility complex Ib (MHC Ib) cell surface protein which performs an essential role in the adaptive immune system. There are several non-classical MHC molecules (including HLA-E, HLA-F, and HLA-G), which have immune regulatory functions. HLA-E, which is encoded by an HLA-E gene (i.e. NCBI Gene ID: 3133), is a heterodimer class Ib molecule that primarily functions as a ligand for the NK cell receptors CD94/NKG2A (NKG2A) and CD94/NKG2C (NKG2C). HLA-E enables NK cells to monitor other MHC class I molecule expression and to tolerate self-expression.

A peptide that binds to HLA-E is one which associates with HLA-E on a cell surface, forming a complex that is capable of interacting with a specific cell receptor on an immune cell. In some embodiments the HLA-E-peptide complex interacts with a NKG2A receptor, a NKG2C receptor, or both. Identification of peptides bound to HLA-E capable of binding to NKG2A or NKG2C has been challenging because of the lack of characterization of the repertoires of HLA-E and NK cell receptors. Further, the large degree of similarity between NKG2A and NKG2C and higher affinity of the inhibitory NKG2A receptor compared to NKG2C have made it especially challenging to generate or identify peptides capable of selectively activating NK cells through NKG2C. These obstacles have been overcome and peptides that are capable of effectively modulating NKG2A+ and/or NKG2C+ cells are disclosed herein.

The development of peptide mimotopes with improved NK cell modulating functions is becoming more important. The synthetic peptides disclosed herein are at least as potent as the endogenous peptides in their combined activation/inhibition potential, and several of the peptides, for the first time, skew NKG2A/NKG2C function, decoupling what has otherwise thus far been a set signaling axis. These peptides may have an even broader utility than analogous T cell modulating peptides, because of the commonality of NK cell signaling. Unlike T cells (which contain essentially uniquely derived receptors in each individual) and their MHC targets (which are sufficiently polymorphic that even the most abundant are present in ~40% of any given population), the NKG2A/C-HLA-E axis is essentially invariant across all humans, making it unique in its scope of applicability.

In some embodiments the peptide is a peptide that modulates NKG2C+ cells. The peptides capable of selectively activating NKG2C+ cells with minimal inhibition of NKG2A+ cells are referred to herein as an NKG2C+ cell activating peptide. These peptides are ligands capable of skewing NK cell activity towards activation. Active NK cells can be utilized to treat diseases such as infectious disease and cancer. For instance, peptides capable of activating and/or expanding NKG2C+ populations could be utilized therapeutically to reduce viral titers or reduce the likelihood and/or severity of latent viral reactivation. Additionally, the activation or expansion of the NKG2C+ population of cells is useful in treating multiple types of cancer, and in particular those cancers with upregulated ligand HLA-E expression, such as colorectal cancer. In another embodiment at least one peptide (SEQ ID NO. 15) capable of affecting NK cell function was a novel CMV-derived peptide, which may be targeted therapeutically to combat CMV infection in particular. At least three peptides (SEQ ID NO.s 2, 3, and 5) showed no or minimal effect on NKG2A+/NKG2C− NK cells, but activate NKG2A−/NKG2C+ cells. SEQ ID NO. 3 demonstrated the strongest activation of NK cells, comparable with the positive control peptides for several markers assessed. Additionally some peptides demonstrated mild inhibitory effects and strong activating effects (including for instance SEQ ID NO. 7, 8, 9 and 10).

In some embodiments, several of the synthetic peptides disclosed herein are associated with stress responses. For example, the peptide of SEQ ID NO. 3 is derived from bifunctional apoptosis regulator protein and the peptide of SEQ ID NO. 7 is derived from cyclic AMP-responsive element-binding protein 3-like protein 1. These peptides may be exploitable as a therapeutic target in stressed cells.

In some embodiments the peptide is a peptide that modulates NKG2A+ cells. The peptides capable of selectively inhibiting NKG2A+ cells with lower or minimal activation of NKG2C+ cells are referred to herein as NKG2A+ cell inhibitory peptides. Inhibition of NK cell activity is useful in the treatment of diseases of self such as autoimmune disorders. Thus, peptides which can inhibit NKG2A+ cells, or inhibit NKG2A+ cells more strongly than they activate NKG2C+ cells, may be utilized to decrease or suppress NK cell responses, such as in the context of autoimmunity or transplantation. An exemplary NKG2A+ cell inhibitory peptide disclosed herein is the peptide of SEQ ID NO. 6.

In some embodiments the peptides are capable of binding to both NKG2A and NKG2C, resulting in activation of NKG2C+ cells and also inhibition of NKG2A+ cells. For instance, peptides of SEQ ID NO. 11, 12, 13, 14, and 15 largely show both strong inhibitory and strong activating effects on NKG2A+/NKG2C− and NKG2A−/NKG2C+ cells, respectively.

In some embodiments each of the peptides disclosed herein may be able to modulate the activities of NKG2A+ or NKG2C+ T cells, in addition to NK cells.

A HLA-E binding peptide as used herein is any peptide that interacts with MHC by binding to HLA-E and modulating NK cells through cell surface receptors. In some embodiments the peptides comprise a sequence of $X_1X_2PX_3RSLX_4X_5$(SEQ ID NO. 1), wherein each X is an amino acid, wherein P is proline, R is Arginine, S is serine, L is Leucine, $X_1$ is Threonine or Valine, $X_2$ is Glycine or Asparagine, $X_3$ is Tryptophan or Glycine, $X_4$ is Tryptophan or Phenylalanine, and $X_5$ is Leucine or Isoleucine. In other embodiments the peptides comprise a sequence of $X_1X_6PX_7RX_8X_9FL$ (SEQ ID NO:4), wherein each X is an amino acid, wherein P is proline, R is Arginine, F is Phenylalanine, L is Leucine, $X_1$ is Threonine or Valine, $X_6$ is Alanine or Asparagine, $X_7$ is Alanine or Glycine, $X_8$ is Serine or Threonine, and $X_9$ is Leucine or Methionine. The peptides may comprise any of the peptides listed in Table 1. Peptides listed in table 1 include but are not limited to TAPARTMFL (SEQ ID NO. 5), VNPGRSLFL (SEQ ID NO. 3), TGPWRSLWI (SEQ ID NO. 2), NMPARTVLF (SEQ ID NO. 6), QMPSRSLLF (SEQ ID NO. 7), TLPKRGLFL (SEQ ID NO. 8), ILTDRSLWL (SEQ ID NO. 9), FLPNRSLLF (SEQ ID NO. 10), TLPERTLYL (SEQ ID NO. 11), VMPGRTLCF (SEQ ID NO. 12), RMPPRSVLL (SEQ ID NO. 13), VMPPRTLLL (SEQ ID NO. 14), and VLPHRTQFL (SEQ ID NO. 15).

In some embodiments, the peptide is 5-30 amino acids in length. The peptide may be for instance, 5-25, 5-20, 5-15, 5-10, 8-30, 8-25, 8-20, 8-15, 8-10, 9-30, 9-29, 9-28, 9-27, 9-26, 9-25, 9-24, 9-23, 9-22, 9-21, 9-20, 9-19, 9-18, 9-17, 9-16, 9-15, 9-14, 9-13, 9-12, 9-11, or 9-10 amino acids in length.

The peptide may be cyclic or linear-non-cyclic. Cyclic peptides in some instances have improved stability properties. Those of skill in the art know how to produce cyclic peptides.

The peptides may also be linked to other molecules. The two or more molecules may be linked directly to one another (e.g., via a peptide bond); linked via a linker molecule, which may or may not be a peptide; or linked indirectly to one another by linkage to a common carrier molecule, for instance.

Thus, linker molecules ("linkers") may optionally be used to link the peptide to another molecule. Linkers may be peptides, which consist of one to multiple amino acids, or non-peptide molecules. Examples of peptide linker molecules useful in the invention include glycine-rich peptide linkers, wherein more than half of the amino acid residues are glycine.

Linker molecules may also include non-peptide or partial peptide molecules. For instance the peptide may be linked to other molecules using well known cross-linking molecules such as glutaraldehyde or EDC (Pierce, Rockford, Illinois). Bifunctional cross-linking molecules are linker molecules that possess two distinct reactive sites. For example, one of the reactive sites of a bifunctional linker molecule may be reacted with a functional group on a peptide to form a covalent linkage and the other reactive site may be reacted with a functional group on another molecule to form a covalent linkage. Homobifunctional cross-linker molecules have two reactive sites which are chemically the same. Examples of homobifunctional cross-linker molecules include, without limitation, glutaraldehyde; N,N'-bis(3-maleimido-propionyl-2-hydroxy-1,3-propanediol (a sulfhydryl-specific homobifunctional cross-linker); certain N-succinimide esters (e.g., discuccinimyidyl suberate, dithiobis (succinimidyl propionate), and soluble bis-sulfonic acid and salt thereof.

The carboxyl terminal amino acid residue of the peptides described herein may also be modified to block or reduce the reactivity of the free terminal carboxylic acid group, e.g., to prevent formation of esters, peptide bonds, and other reactions. Such blocking groups include forming an amide of the carboxylic acid group. Other carboxylic acid groups that may be present in polypeptide may also be blocked, again provided such blocking does not elicit an undesired immune reaction or significantly alter the capacity of the peptide to specifically function.

The peptide for instance, may be linked to a PEG molecule. Such a molecule is referred to as a PEGylated peptide.

The invention further provides derivatives (including but not limited to fragments), and analogs of the peptides set forth in Table 1. The production and use of derivatives and analogs related to peptides are within the scope of the present invention. In a specific embodiment, the derivative or analog is functionally active, i.e., capable of exhibiting one or more functional activities associated with a peptide of Table 1.

In particular, the peptide derivatives can be made by altering peptide sequences by substitutions, insertions or deletions that provide for functionally equivalent molecules. The peptide derivatives of the invention include, but are not limited to, those containing, as a primary amino acid sequence, all or part of the amino acid sequence of a peptides including altered sequences in which functionally equivalent amino acid residues are substituted for residues within the sequence resulting in a silent change (i.e., conservative substitutions). For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Peptide derivatives of the invention also include, but are not limited to, those containing, as a primary amino acid sequence, all or part of the amino acid sequence of a peptide including altered sequences in which amino acid residues are substituted for residues with similar chemical properties (i.e., conservative substitutions). In specific embodiments, 1, 2, 3, 4, or 5 amino acids are substituted.

Derivatives or analogs of the peptides include, but are not limited to, those peptides which are substantially homologous to the peptides or fragments thereof. Furthermore, if desired, nonclassical amino acids or chemical amino acid analogs can be introduced as a substitution or addition into the peptide sequence. Non-classical amino acids include, but are not limited to, the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

Included within the scope of the invention are peptides having at least 70% sequence identity with any of the peptides disclosed herein. In some embodiments the peptides comprises an amino acid sequence at least 80%, at least 85%, at least 90%, at least 95%, at least 96%, at least 97%, at least 98%, or at least 99% identical to an amino acid sequence of any one of the sequences provided herein.

The term "identity" refers to a relationship between the sequences of two or more polypeptides, as determined by comparing the sequences. Identity also refers to the degree of sequence relatedness between or among sequences as determined by the number of matches between strings of two or more amino acid residues. Identity measures the percent of identical matches between the smaller of two or more sequences with gap alignments (if any) addressed by a particular mathematical model or computer program (e.g., "algorithms"). Identity of related peptides can be readily calculated by known methods. "Percent (%) identity" as it applies to polypeptide sequences is defined as the percentage of residues (amino acid residues) in the candidate amino acid sequence that are identical with the residues in the amino acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polypeptide as determined by sequence alignment programs and parameters described herein and known to those skilled in the art. For instance, a Fast Optimal Global Sequence Alignment Algorithm (FOGSAA) has been developed that purportedly produces global alignment of protein sequences faster than other optimal global alignment methods, including the Needleman-Wunsch algorithm.

The peptide sequences disclosed herein can be characterized by a hydrophilicity analysis (Hopp, T. and Woods, K., 1981, Proc. Natl. Acad. Sci. U.S.A. 78: 3824). A hydrophilicity profile can be used to identify the hydrophobic and hydrophilic regions of the peptides. Secondary structural analysis (Chou, P. and Fasman, G., 1974, Biochemistry 13: 222) can also be done, to identify regions of the peptides that assume specific secondary structures. Other methods of structural analysis can also be employed. These include, but are not limited to, X-ray crystallography (Engstom, A., 1974, Biochem. Exp. Biol. 11: 7-13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.). The functional activity of a peptide or a fragment thereof can be assayed by various methods known in the art.

The peptides useful herein are isolated peptides. As used herein, the term "isolated" means that the referenced material is removed from its native environment, e.g., a cell. Thus, an isolated biological material can be free of some or all cellular components, i.e., components of the cells in which the native material is occurs naturally (e.g., cytoplasmic or membrane component). The isolated peptides may be substantially pure and essentially free of other substances with which they may be found in nature or in vivo systems to an extent practical and appropriate for their intended use. In particular, the peptides are sufficiently pure and are sufficiently free from other biological constituents of their hosts cells so as to be useful in, for example, producing pharmaceutical preparations or sequencing. Because an isolated peptide of the invention may be admixed with a pharmaceutically acceptable carrier in a pharmaceutical preparation, the peptide may comprise only a small percentage by weight of the preparation. The peptide is nonetheless substantially pure in that it has been substantially separated from at least one of the substances with which it may be associated in living systems.

The term "purified" in reference to a protein, refers to the separation of the desired substance from contaminants to a degree sufficient to allow the practitioner to use the purified substance for the desired purpose. Preferably this means at least one order of magnitude of purification is achieved, more preferably two or three orders of magnitude, most preferably four or five orders of magnitude of purification of the starting material or of the natural material. In specific embodiments, a purified peptide is at least 60%, at least 80%, or at least 90% of total protein in a composition, as the case may be, by weight. In a specific embodiment, a purified peptide is purified to homogeneity as assayed by, e.g., sodium dodecyl sulfate polyacrylamide gel electrophoresis, or agarose gel electrophoresis.

The peptides bind to HLA-E, preferably in a selective manner. As used herein, the terms "selective binding" and "specific binding" are used interchangeably to refer to the ability of the peptide to bind with greater affinity to HLA-E and fragments thereof than to unrelated proteins.

Peptides can be tested for their ability to bind to HLA-E using standard binding assays known in the art or the assays experimental and computational described in the examples. As an example of a suitable assay, HLA-E can be immobilized on a surface (such as in a well of a multi-well plate) and then contacted with a labeled peptide. The amount of peptide that binds to the HLA-E (and thus becomes itself immobilized onto the surface) may then be quantitated to determine whether a particular peptide binds to HLA-E. Alternatively, the amount of peptide not bound to the surface may also be measured. In a variation of this assay, the peptide can be tested for its ability to bind directly to a HLA-E-expressing cell.

Compounds for use in therapy can be tested in suitable animal model systems prior to testing in humans, including but not limited to in rats, mice, chicken, cows, monkeys, rabbits, etc. Further, any assays known to those skilled in the art can be used to evaluate the prophylactic and/or therapeutic utility of the combinatorial therapies disclosed herein for treatment or prevention of cancer and/or infectious diseases, as well as autoimmune disease and transplant rejection therapies.

In one embodiment, the methods described herein are useful in treating an autoimmune disease in a subject by administering therapeutically effective amount of a NKG2A+ cell inhibitory peptide to the subject, wherein the NKG2A+ cell inhibitory peptide comprises a sequence having at least 80% sequence identity to NMPARTVLF (SEQ ID NO. 6). NK cell activation is determined by a balance of cell-surface receptors that have either activating or inhibitory properties. One way NK cells modulate their activity is through receptors CD94/NKG2A (NKG2A) and CD94/NKG2C (NKG2C). Both NKG2A and NKG2C bind to the highly conserved class Ib MHC HLA-E complexed with a peptide. Modulation in NK activity has important implications for innate and adaptive immune responses.

In addition to direct cytotoxicity, activated NK cells exert innate and adaptive immunoregulatory functions by releasing cytokines and chemokines such as interferon (IFN)-γ, tumor necrosis factor (TNF)-α, granulocyte-macrophage colony-stimulating factor (GM-CSF), and chemokine (C-C motif) ligand (CCL)5. Cytokines secreted by NK cells can recruit and activate other immune cells such as macrophages, neutrophils, and autoreactive T and B cells, thereby indirectly enhancing inflammation and tissue damage. Autoimmune diseases typically develop through abnormal activation of T and B cells; however, increasing evidence supports that NK cells—which link innate and adaptive immunity—play an important role in autoimmunity.

Thus, inhibition of NK cell activity in the methods described are useful for treating autoimmune diseases such as multiple sclerosis, systemic lupus erythematosus, inflammatory bowel disease, rheumatoid arthritis, Graves' disease, autoimmune thyroiditis, autoimmune myositis, discoid lupus erythematosus, Crohns disease, Sjogren's syndrome, Reiter's syndrome, Rheumatoid arthritis, myasthenia gravis, Kawasaki's disease, Celiac disease, Goodpasture's syndrome, or aplastic anemia.

"Autoimmune Disease" refers to those diseases which are commonly associated with the nonanaphylactic hypersensitivity reactions (Type II, Type III and/or Type IV hypersensitivity reactions) that generally result because of the subject's own humoral and/or cell-mediated immune response to one or more immunogenic substances of endogenous and/or exogenous origin. Such autoimmune diseases are distinguished from diseases associated with the anaphylactic (Type I or IgE-mediated) hypersensitivity reactions.

Additional embodiments may be used to modulate the activities of NKG2A+ or NKG2C+ T cells.

In some embodiments, the present invention provides a method of treating a cancer comprising administering to a subject in whom such treatment is desired a therapeutically effective amount of a NKG2C+ cell activating peptide, wherein the NKG2C+ cell activating peptide comprises a sequence having at least 80% sequence identity to a sequence selected from TAPARTMFL (SEQ ID NO. 5), VNPGRSLFL (SEQ ID NO. 3), TGPWRSLWI (SEQ ID NO. 2), QMPSRSLLF (SEQ ID NO. 7), TLPKRGLFL (SEQ ID NO. 8), ILTDRSLWL (SEQ ID NO. 9), and FLPNRSLLF (SEQ ID NO. 10). Without be bound by theory, the applicant believes the NKG2C+ cell activating peptides induce NK cells host immunity against cancer by exerting cytotoxicity and secreting a wide variety of cytokines to inhibit tumor progression.

Natural killer (NK) cells are important innate immune cells that provide a first-line defense against carcinogenesis and are closely related to cancer development. NK cell effector functions are regulated by opposing signals from activating and inhibitory receptors and determine NK cell activity against tumor targets. However, NK cells are functionally suppressed owing to multiple immunosuppressive factors in the tumor microenvironment; thus, releasing the suppressed state of NK cells is an emergent project and a promising solution for immunotherapy. NK cell cytotoxicity requires successful activation events that begin with NK cell adhesion to a tumor target cell and culminate in the release of cytotoxic granules. Additional properties unique to NK cells include a capacity to enhance antibody and T cell responses which is a valuable tool in cancer immunotherapies.

A composition of the invention may, for example, be used as a first, second, third or fourth line cancer treatment. In some embodiments, the invention provides methods for treating a cancer (including ameliorating a symptom thereof) in a subject refractory to one or more conventional therapies for such a cancer, said methods comprising administering to said subject a therapeutically effective amount of a composition comprising a NKG2C+ cell activating peptide.

A cancer may be determined to be refractory to a therapy when at least some significant portion of the cancer cells are not killed or their cell division are not arrested in response to the therapy. Such a determination can be made either in vivo or in vitro by any method known in the art for assaying the effectiveness of treatment on cancer cells, using the art-accepted meanings of “refractory” in such a context. In a specific embodiment, a cancer is refractory where the number of cancer cells has not been significantly reduced, or has increased.

The invention provides methods for treating a cancer (including ameliorating one or more symptoms thereof) in a subject refractory to existing single agent therapies for such a cancer, said methods comprising administering to said subject a therapeutically effective amount of a composition comprising a NKG2C+ cell activating peptide and a therapeutically effective amount of one or more therapeutic agents other than the NKG2C+ cell activating peptide. The invention also provides methods for treating cancer by administering a composition comprising a NKG2C+ cell activating peptide in combination with any other anti-cancer treatment (e.g., radiation therapy, chemotherapy, or surgery) to a patient who has proven refractory to other treatments. The invention also provides methods for the treatment of a patient having cancer and immunosuppressed by reason of having previously undergone one or more other cancer therapies. The invention also provides alternative methods for the treatment of cancer where chemotherapy, radiation therapy, hormonal therapy, and/or biological therapy/immunotherapy has proven or may prove too toxic, i.e., results in unacceptable or unbearable side effects, for the subject being treated.

Cancers that can be treated by the methods encompassed by the invention include, but are not limited to, neoplasms, malignant tumors, metastases, or any disease or disorder characterized by uncontrolled cell growth such that it would be considered cancerous. The cancer may be a primary or metastatic cancer. Specific cancers that can be treated according to the present invention include, but are not limited to, those listed below.

Cancers include, but are not limited to, biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen’s disease and Paget’s disease; liver cancer; lung cancer; lymphomas including Hodgkin’s disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi’s sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms’ tumor. Commonly encountered cancers include breast, prostate, lung, ovarian, colorectal, and brain cancer. In some embodiments the cancer is a cancer having upregulated HLA-E expression, such as colorectal cancer.

In a specific embodiment, leukoplakia, a benign-appearing hyperplastic or dysplastic lesion of the epithelium, or Bowen’s disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

The prophylactic use of the compositions of the invention is also indicated in some viral infections that may lead to cancer. For example, human papilloma virus can lead to cervical cancer (see, e.g., Hernandez-Avila et al., Archives of Medical Research (1997) 28: 265-271), Epstein-Barr virus (EBV) can lead to lymphoma (see, e.g., Herrmann et al., J Pathol (2003) 199(2): 140-5), hepatitis B or C virus can lead to liver carcinoma (see, e.g., El-Serag, J Clin Gastroenterol (2002) 35(5 Suppl 2): S72-8), human T cell leukemia virus (HTLV)-I can lead to T-cell leukemia (see e.g., Mortreux et al., Leukemia (2003) 17(1): 26-38), and human herpesvirus-8 infection can lead to Kaposi’s sarcoma (see, e.g., Kadow et al., Curr Opin Investig Drugs (2002) 3(11): 1574-9).

In one set of embodiments, the invention includes a method of treating a subject susceptible to or exhibiting symptoms of cancer. The cancer may be primary, metastatic, recurrent, or multi-drug resistant. In some cases, the cancer is drug-resistant or multi-drug resistant. As used herein, a “drug-resistant cancer” is a cancer that is resistant to conventional commonly-known cancer therapies. Examples of conventional cancer therapies include treatment of the cancer with agents such as methotrexate, trimetrexate, adriamycin, taxotere, doxorubicin, 5-flurouracil, vincristine, vinblastine, pamidronate disodium, anastrozole, exemestane, cyclophosphamide, epirubicin, toremifene, letrozole, trastuzumab, megestrol, tamoxifen, paclitaxel, docetaxel, capecitabine, goserelin acetate, etc. A "multi-drug resistant cancer" is a cancer that resists more than one type or class of cancer agents, i.e., the cancer is able to resist a first drug having a first mechanism of action, and a second drug having a second mechanism of action.

One component of the invention involves promoting an enhanced immune response against the cancer by administering the compounds of the invention. The compounds may be administered in conjunction with a cancer antigen to further promote a cancer specific immune response. A "cancer antigen" as used herein is a compound, such as a peptide or carbohydrate, associated with a tumor or cancer cell surface and which can provoke an immune response when expressed on the surface of an antigen presenting cell in the context of an MHC molecule. Preferably, the antigen is expressed at the cell surface of the cancer cell. Even more preferably, the antigen is one which is not expressed by normal cells, or at least not expressed to the same level as in cancer cells. For example, some cancer antigens are normally silent (i.e., not expressed) in normal cells, some are expressed only at certain stages of differentiation and others are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. The differential expression of cancer antigens in normal and cancer cells can be exploited to target cancer cells. As used herein, the terms "cancer antigen" and "tumor antigen" are used interchangeably.

Another form of anti-cancer therapy involves administering an antibody specific for a cell surface antigen of, for example, a cancer cell. In one embodiment, the antibody may be selected from the group consisting of Ributaxin, Herceptin, Rituximab, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA. Other antibodies include but are not limited to anti-CD20 antibodies, anti-CD40 antibodies, anti-CD19 antibodies, anti-CD22 antibodies, anti-HLA-DR antibodies, anti-CD80 antibodies, anti-CD86 antibodies, anti-CD54 antibodies, and anti-CD69 antibodies. These antibodies are available from commercial sources or may be synthesized de novo.

In one embodiment, the methods of the invention can be used in conjunction with one or more other forms of cancer treatment, for example, in conjunction with an anti-cancer agent, chemotherapy, radiotherapy, etc. (e.g., simultaneously, or as part of an overall treatment procedure). The term "cancer treatment" as used herein, may include, but is not limited to, chemotherapy, radiotherapy, adjuvant therapy, vaccination, or any combination of these methods. Parameters of cancer treatment that may vary include, but are not limited to, dosages, timing of administration or duration or therapy; and the cancer treatment can vary in dosage, timing, or duration. Another treatment for cancer is surgery, which can be utilized either alone or in combination with any of the previously treatment methods. Any agent or therapy (e.g., chemotherapies, radiation therapies, surgery, hormonal therapies, and/or biological therapies/immunotherapies) which is known to be useful, or which has been used or is currently being used for the prevention or treatment of cancer can be used in combination with a composition of the invention in accordance with the invention described herein. One of ordinary skill in the medical arts can determine an appropriate treatment for a subject.

Examples of such agents (i.e., anti-cancer agents) include, but are not limited to, DNA-interactive agents including, but not limited to, the alkylating agents (e.g., nitrogen mustards, e.g. Chlorambucil, Cyclophosphamide, Isofamide, Mechlorethamine, Melphalan, Uracil mustard; Aziridine such as Thiotepa; methanesulphonate esters such as Busulfan; nitroso ureas, such as Carmustine, Lomustine, Streptozocin; platinum complexes, such as Cisplatin, Carboplatin; bioreductive alkylator, such as Mitomycin, and Procarbazine, Dacarbazine and Altretamine); the DNA strand-breakage agents, e.g., Bleomycin; the intercalating topoisomerase II inhibitors, e.g., Intercalators, such as Amsacrine, Dactinomycin, Daunorubicin, Doxorubicin, Idarubicin, Mitoxantrone, and nonintercalators, such as Etoposide and Teniposide; the nonintercalating topoisomerase II inhibitors, e.g., Etoposide and Teniposde; and the DNA minor groove binder, e.g., Plicamydin; the antimetabolites including, but not limited to, folate antagonists such as Methotrexate and trimetrexate; pyrimidine antagonists, such as Fluorouracil, Fluorodeoxyuridine, CB3717, Azacitidine and Floxuridine; purine antagonists such as Mercaptopurine, 6-Thioguanine, Pentostatin; sugar modified analogs such as Cytarabine and Fludarabine; and ribonucleotide reductase inhibitors such as hydroxyurea; tubulin Interactive agents including, but not limited to, colcbicine, Vincristine and Vinblastine, both alkaloids and Paclitaxel and cytoxan; hormonal agents including, but not limited to, estrogens, conjugated estrogens and Ethinyl Estradiol and Diethylstilbesterol, Chlortrianisen and Idenestrol; progestins such as Hydroxyprogesterone caproate, Medroxyprogesterone, and Megestrol; and androgens such as testosterone, testosterone propionate; fluoxymesterone, methyltestosterone; adrenal corticosteroid, e.g., Prednisone, Dexamethasone, Methylprednisolone, and Prednisolone; leutinizing hormone releasing hormone agents or gonadotropin-releasing hormone antagonists, e.g., leuprolide acetate and goserelin acetate; antihormonal antigens including, but not limited to, antiestrogenic agents such as Tamoxifen, antiandrogen agents such as Flutamide; and antiadrenal agents such as Mitotane and Aminoglutethimide; cytokines including, but not limited to, IL-1.alpha, IL-1β, IL-2, IL-3, IL-4, IL-5, IL-6, IL-7, IL-8, IL-9, IL-10, IL-11, IL-12, IL-13, IL-18, TGF-β, GM-CSF, M-CSF, G-CSF, TNF-α, TNF-β, LAF, TCGF, BCGF, TRF, BAF, BDG, MP, LIF, OSM, TMF, PDGF, IFN-α, IFN-β, IFN-γ, and Uteroglobins (U.S. Pat. No. 5,696,092); anti-angiogenics including, but not limited to, agents that inhibit VEGF (e.g., other neutralizing antibodies (Kim et al., 1992; Presta et al., 1997; Sioussat et al., 1993; Kondo et al., 1993; Asano et al., 1995, U.S. Pat. No. 5,520,914), soluble receptor constructs (Kendall and Thomas, 1993; Aiello et al., 1995; Lin et al., 1998; Millauer et al., 1996), tyrosine kinase inhibitors (Siemeister et al., 1998, U.S. Pat. Nos. 5,639,757, and 5,792,771), antisense strategies, RNA aptamers and ribozymes against VEGF or VEGF receptors (Saleh et al., 1996; Cheng et al., 1996; Ke et al., 1998; Parry et al., 1999); variants of VEGF with antagonistic properties as described in WO 98/16551;

compounds of other chemical classes, e.g., steroids such as the angiostatic 4,9(11)-steroids and C21-oxygenated steroids, as described in U.S. Pat. No. 5,972,922; thalidomide and related compounds, precursors, analogs, metabolites and hydrolysis products, as described in U.S. Pat. Nos. 5,712,291 and 5,593,990; Thrombospondin (TSP-1) and platelet factor 4 (PF4); interferons and metalloproteinsase inhibitors; tissue inhibitors of metalloproteinases (TIMPs); anti-Invasive Factor, retinoic acids and paclitaxel (U.S. Pat. No. 5,716,981); AGM-1470 (Ingber et al., 1990); shark cartilage extract (U.S. Pat. No. 5,618,925); anionic polyamide or polyurea oligomers (U.S. Pat. No. 5,593,664); oxindole derivatives (U.S. Pat. No. 5,576,330); estradiol derivatives (U.S. Pat. No. 5,504,074); thiazolopyrimidine derivatives (U.S. Pat. No. 5,599,813); and LM609 (U.S. Pat. No. 5,753,230); apoptosis-inducing agents including, but not limited to, bcr-abl, bcl-2 (distinct from bcl-1, cyclin D1; GenBank accession numbers M14745, X06487; U.S. Pat. Nos. 5,650,491; and 5,539,094) and family members including Bcl-x1, Mcl-1, Bak, A1, A20, and antisense nucleotide sequences (U.S. Pat. Nos. 5,650,491; 5,539,094; and 5,583,034); Immunotoxins and coaguligands, tumor vaccines, and antibodies.

Specific examples of anti-cancer agents which can be used in accordance with the methods of the invention include, but not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; angiogenesis inhibitors; anti-dorsalizing morphogenetic protein-1; ara-CDP-DL-PTBA; BCR/ABL antagonists; CaRest M3; CARN 700; casein kinase inhibitors (ICOS); clotrimazole; collismycin A; collismycin B; combretastatin A4; crambescidin 816; cryptophycin 8; curacin A; dehydrodidemnin B; didemnin B; dihydro-5-azacytidine; dihydrotaxol, duocarmycin SA; kahalalide F; lamellarin-N triacetate; leuprolide+estrogen+progesterone; lissoclinamide 7; monophosphoryl lipid A+myobacterium cell wall sk; N-acetyldinaline; N-substituted benzamides; O6-benzylguanine; placetin A; placetin B; platinum complex; platinum compounds; platinum-triamine complex; rhenium Re 186 etidronate; RII retinamide; rubiginone B 1; SarCNU; sarcophytol A; sargramostim; senescence derived inhibitor 1; spicamycin D; tallimustine; 5-fluorouracil; thrombopoietin; thymotrinan; thyroid stimulating hormone; variolin B; thalidomide; velaresol; veramine; verdins; verteporfin; vinorelbine; vinxaltine; vitaxin; zanoterone; zeniplatin; and zilascorb.

The invention also encompasses administration of a composition comprising NKG2C+ cell activating peptide in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radioactive source is placed inside the body close to cancer cells or a tumor mass.

In specific embodiments, an appropriate anti-cancer regimen is selected depending on the type of cancer. For instance, a patient with ovarian cancer may be administered a therapeutically effective amount of a composition comprising NKG2C+ cell activating peptide in combination with a therapeutically effective amount of one or more other agents useful for ovarian cancer therapy, including but not limited to, intraperitoneal radiation therapy, such as P32 therapy, total abdominal and pelvic radiation therapy, cisplatin, the combination of paclitaxel (Taxol) or docetaxel (Taxotere) and cisplatin or carboplatin, the combination of cyclophosphamide and cisplatin, the combination of cyclophosphamide and carboplatin, the combination of 5-FU and leucovorin, etoposide, liposomal doxorubicin, gemcitabine or topotecan. In a particular embodiment, a therapeutically effective amount of a composition of the invention is administered in combination with the administration of Taxol for patients with platinum-refractory disease. A further embodiment is the treatment of patients with refractory cancer including administration of: ifosfamide in patients with disease that is platinum-refractory, hexamethylmelamine (HMM) as salvage chemotherapy after failure of cisplatin-based combination regimens, and tamoxifen in patients with detectable levels of cytoplasmic estrogen receptor on their tumors.

In some embodiments the peptides present a new avenue for activating and potentially expanding NKG2C+NK cells in vivo or ex vivo. Thus, cells carrying the peptide in the context of HLA-E are encompassed herein. Methods of using such cells are also included within the invention.

In certain embodiments, the peptides are formulated as pharmaceutical compositions and may comprise, for example, at least about 0.1% of an active compound. In other embodiments, an active compound may comprise between about 2% to about 75% of the weight of the unit, or between about 25% to about 60%, for example, and any range derivable therein.

Subject doses of the compounds described herein typically range from about 0.1 μg to 10,000 mg, more typically from about 1 μg/day to 8000 mg, and most typically from about 10 g to 100 μg. Stated in terms of subject body weight, typical dosages range from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the molecules of the invention are also contemplated. In some instances, when the molecules of the invention are administered with another therapeutic, for instance, an anti-viral agent a sub-therapeutic dosage of either the molecules or the anti-viral agent, or a sub-therapeutic dosage of both, is used in the treatment of a subject having, or at risk of developing, a viral infection. When the two classes of drugs are used together, the anti-viral agent may be administered in a sub-therapeutic dose to produce a desirable therapeutic result. A "sub-therapeutic dose" as used herein refers to a dosage which is less than that dosage which would produce a therapeutic result in the subject if administered in the absence of the other agent. Thus, the sub-therapeutic dose of an anti-viral agent is one which would not produce the desired therapeutic result in the subject in the absence of the administration of the molecules of the invention. Therapeutic doses of an anti-viral agents are well known in the field of medicine for the treatment of viral infection.

Pharmaceutically acceptable carriers include diluents, fillers, salts, buffers, stabilizers, solubilizers and other materials which are well-known in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids, such as a syrup, an elixir or an emulsion.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible nanoparticle, microparticle or implant that is suitable for implantation into the mammalian recipient. A polymeric matrix may be used to achieve sustained release of the agent in a subject. In accordance with one aspect of the instant invention, the agent described herein may be encapsulated or dispersed within the biocompatible, preferably biodegradable polymeric matrix. Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the compound, increasing convenience to the subject and the physician.

EXAMPLES

Example 1: Identification of Novel Peptides Capable of Binding to HLA-E Affecting NK Cell Activity Via NKG2A and/or NKG2C A human immortalized myelogenous leukemia cell line (K562), which expresses HLA-E was incubated with novel peptides (Table 1) derived from the human proteome or human cytomegalovirus proteome. The effects of the peptides on NK cell selective inhibition (Tables 2-5) and/or activation (Tables 6-9) were determined by measuring four markers of NK cell activation (CD107a, IFNG, TNF, CCL3) in NKG2A+/NKG2C− and NKG2A−/NKG2C+NK cells. Controls assessments were also performed using NKG2A−/NKG2C− cells (Tables 10-13). Inhibition was indicated by a decrease in percent cells positive for cell surface markers, while activation was indicated by an increase in percent cells positive for cell surface markers. The average level of activation for the negative control peptide (VMAPQSLLL, "PQS" (SEQ ID NO: 17)) is shown as a dashed line (FIGS. 1A-1L). Three peptides (h3, h5, h13) showed no effect on NKG2A+/NKG2C− NK cell inhibition (FIGS. 1A-1D) but activated NKG2A−/NKG2C+ cells (FIGS. 1E-1H). Additional peptides (h1, h2, h4, h8) showed mild inhibitory effects on NKG2A+/NKG2C− NK cells (FIGS. 1A-1D) and strong activating effects on NKG2A−/NKG2C+NK cells (FIGS. 1E-1H). The remaining peptides (h7, h1, h12, h14, h15, CMV1) showed both strong inhibitory and activating effects on NKG2A+/NKG2C− (FIGS. 1A-1D) and NKG2A−/NKG2C+NK cells (FIGS. 1E-1H), respectively. All peptides had no effect on activation or inhibition on control NKG2A−/NKG2C− NK cells (FIGS. 1I-1L).

TABLE 1

Peptides which affect NK cell activity.

| Name | Peptide | SEQ ID NO: |
|---|---|---|
| $CREB3L1_{419-427}$ (human1) | QMPSRSLLF | 7 |
| $AKAP6_{388-396}$ (human2) | TLPKRGLFL | 8 |
| $GTF3C5_{293-301}$ (human3) | TGPWRSLWI | 2 |
| $FBXO41_{670-678}$ (human4) | ILTDRSLWL | 9 |
| $BFAR_{263-271}$ (human5) | VNPGRSLFL | 3 |
| $ECEL1_{269-277}$ (human7) | TLPERTLYL | 11 |
| $SLC52A3_{354-362}$ (human8) | FLPNRSLLF | 10 |
| $TACR3_{226-234}$ (human11) | VMPGRTLCF | 12 |
| $INTS1_{260-268}$ (human12) | RMPPRSVLL | 13 |
| $PISD_{55-63}$ (human13) | TAPARTMFL | 5 |
| $MTREX_{490-498}$ (human14) | NMPARTVLF | 6 |
| $HLA\text{-}A_{3-11}$ (human15) | VMPPRTLLL | 14 |
| $UL120_{72-80}$, Merlin (CMV1) | VLPHRTQFL | 15 |

TABLE 2

Effects of novel peptides on NKG2A+/NKG2C- inhibition through a reduction in percentage of CD107a+ NK cells.

| Peptide | Trial 1 | Trial 2 | Trial 3 | Trial 4 | Trial 5 | Trial 6 |
|---|---|---|---|---|---|---|
| VMAPQSLLL (PQS) (SEQ ID NO: 17) | 29.1 | 47.4 | 46.5 | 40.7 | 30.1 | 24.4 |
| VMAPRTLFL (LFL) (SEQ ID NO: 18) | 1.67 | 0.52 | 1.39 | 3.73 | 4.49 | 3.12 |
| VMAPRTLIL (LIL) (SEQ ID NO: 19) | 0.35 | 2.73 | 1.95 | 0.77 | 0.56 | 0.92 |
| human1 | 15.3 | 25.7 | 28.5 | 14.6 | 9.4 | 13.3 |
| human2 | 10.8 | 13 | 16.7 | 15.1 | 14.4 | 14 |
| human3 | 34.8 | 47.2 | 44.9 | 37.7 | 35.9 | 25.7 |
| human4 | 16.9 | 23.7 | 22 | 15 | 14.8 | 12.8 |
| human5 | 36.8 | 48.4 | 43.1 | 33.4 | 30.4 | 26 |
| human7 | 0.52 | 0.72 | 0.59 | 0.71 | 0.64 | 1.96 |
| human8 | 19.1 | 26.4 | 27.5 | 28.2 | 17.7 | 20 |
| human11 | 0.35 | 1.08 | 1.25 | 1.09 | 0.66 | 1.02 |
| human12 | 0.85 | 0.99 | 1.25 | | | |

TABLE 2-continued

Effects of novel peptides on NKG2A+/NKG2C- inhibition through a reduction in percentage of CD107a+ NK cells.

| Peptide | Trial 1 | Trial 2 | Trial 3 | Trial 4 | Trial 5 | Trial 6 |
|---|---|---|---|---|---|---|
| human13 | 31.2 | 50.6 | 44.4 | 37.6 | 32.2 | 28.2 |
| human14 | 1.54 | 2.38 | 3.66 | 2.52 | 4.05 | 1.16 |
| human15 | 0.49 | 0.79 | 0.73 | 0.75 | 1.04 | 0.52 |
| CMV1 | 2.12 | 3.42 | 4.2 | 3.15 | 3.92 | 2.27 |

TABLE 3

Effects of novel peptides on NKG2A+/NKG2C- inhibition through a reduction in percentage of IFNG+ NK cells.

| Peptide | Trial 1 | Trial 2 | Trial 3 | Trial 4 | Trial 5 | Trial 6 |
|---|---|---|---|---|---|---|
| VMAPQSLLL (PQS) (SEQ ID NO: 17) | 10.1 | 27.3 | 35.1 | 23.1 | 14.1 | 8.37 |
| VMAPRTLFL (LFL) (SEQ ID NO: 18) | 0.22 | 0.21 | 0.94 | 0.71 | 1.92 | 0.29 |
| VMAPRTLIL (LIL) (SEQ ID NO: 19) | 0 | 0.59 | 0.87 | 0.08 | 0.06 | 0.05 |
| human1 | 4.26 | 9.68 | 15.5 | 3.06 | 2.48 | 2.26 |
| human2 | 2.35 | 2.85 | 7.56 | 2.41 | 5.78 | 3.48 |
| human3 | 15.5 | 26.8 | 32.1 | 20.1 | 19.2 | 9.52 |
| human4 | 5.47 | 8.81 | 13.3 | 3.31 | 6.82 | 3.02 |
| human5 | 16.9 | 28.8 | 30.8 | 17.9 | 16.5 | 10.5 |
| human7 | 0.13 | 0.21 | 0.49 | 0.16 | 0.28 | 0.67 |
| human8 | 5.56 | 10.5 | 14.7 | 12.7 | 7.1 | 6.74 |
| human11 | 0.13 | 0.53 | 0.6 | 0.29 | 0.09 | 0.05 |
| human12 | 0.14 | 0.32 | 0.65 | | | |
| human13 | 13 | 30.8 | 31.7 | 21.7 | 16.9 | 8.81 |
| human14 | 0.3 | 0.79 | 2.62 | 0.83 | 2.12 | 0.43 |
| human15 | 0.05 | 0.3 | 0.44 | 0.2 | 0.19 | 0.24 |
| CMV1 | 0.46 | 1.08 | 2.52 | 0.93 | 1.35 | 0.82 |

TABLE 4

Effects of novel peptides on NKG2A+/NKG2C- inhibition through a reduction in percentage of TNF+ NK cells.

| Peptide | Trial 1 | Trial 2 | Trial 3 | Trial 4 | Trial 5 | Trial 6 |
|---|---|---|---|---|---|---|
| VMAPQSLLL (PQS) (SEQ ID NO: 17) | 2.95 | 13.3 | 18.8 | 11.6 | 6.1 | 4.14 |
| VMAPRTLFL (LFL) (SEQ ID NO: 18) | 0.08 | 0.07 | 0.5 | 0.32 | 0.72 | 0.19 |
| VMAPRTLIL (LIL) (SEQ ID NO: 19) | 0 | 0.39 | 0.46 | 0.08 | 0.06 | 0.05 |

TABLE 4-continued

Effects of novel peptides on NKG2A+/NKG2C- inhibition through a reduction in percentage of TNF+ NK cells.

| Peptide | Trial 1 | Trial 2 | Trial 3 | Trial 4 | Trial 5 | Trial 6 |
|---|---|---|---|---|---|---|
| human1 | 1.66 | 3.94 | 9.23 | 2.61 | 1.56 | 1.77 |
| human2 | 0.83 | 1.25 | 3.94 | 1.74 | 2.47 | 2.18 |
| human3 | 6.18 | 12.4 | 19.7 | 12.5 | 9.62 | 5.43 |
| human4 | 1.97 | 4.06 | 7.29 | 2.82 | 3.39 | 2.79 |
| human5 | 7.26 | 14.6 | 19.4 | 10.7 | 7.74 | 6.36 |
| human7 | 0.05 | 0.11 | 0.1 | 0.08 | 0.18 | 0.38 |
| human8 | 1.84 | 4.8 | 6.96 | 7.59 | 3.6 | 4.07 |
| human11 | 0.05 | 0.21 | 0.35 | 0.23 | 0 | 0 |
| human12 | 0.03 | 0.17 | 0.45 | | | |
| human13 | 3.99 | 13.8 | 17 | 12.6 | 7.45 | 5.68 |
| human14 | 0.12 | 0.31 | 1.09 | 0.55 | 0.89 | 0.14 |
| human15 | 0.01 | 0.27 | 0.19 | 0.18 | 0.16 | 0.05 |
| CMV1 | 0.27 | 0.39 | 1.09 | 0.7 | 0.82 | 0.34 |

TABLE 5

Effects of novel peptides on NKG2A+/NKG2C- inhibition through a reduction in percentage of CCL3+ NK cells.

| Peptide | Trial 1 | Trial 2 | Trial 3 | Trial 4 | Trial 5 | Trial 6 |
|---|---|---|---|---|---|---|
| VMAPQSLLL (PQS) (SEQ ID NO: 17) | 49.8 | 70.6 | 58.2 | 50.7 | 47.7 | 31.3 |
| VMAPRTLFL (LFL) (SEQ ID NO: 18) | 9.62 | 1.44 | 1.79 | 7.27 | 19.9 | 4.24 |
| VMAPRTLIL (LIL) (SEQ ID NO: 19) | 1.59 | 14.4 | 4.32 | 0.75 | 1.56 | 0.92 |
| human1 | 31.8 | 47 | 28.8 | 14.2 | 25.5 | 16.6 |
| human2 | 17.5 | 34.9 | 17.3 | 13.3 | 29.3 | 16.2 |
| human3 | 54.6 | 73.9 | 55.1 | 46.5 | 49.6 | 33.1 |
| human4 | 35.5 | 56.4 | 34.7 | 16.1 | 32.7 | 13.4 |
| human5 | 51.6 | 71.6 | 55.3 | 40.9 | 44.2 | 33.1 |
| human7 | 1.37 | 1.85 | 1.62 | 0.64 | 1.26 | 2.68 |
| human8 | 39.5 | 56 | 38.2 | 32.8 | 33.3 | 27.1 |
| human11 | 4.05 | 7.9 | 3.93 | 1.77 | 2.68 | 1.02 |
| human12 | 1.94 | 2.96 | 2.9 | | | |
| human13 | 52.5 | 75.9 | 52.6 | 47.3 | 48.9 | 39.3 |
| human14 | 3.55 | 6.94 | 6.08 | 3.51 | 17 | 2.66 |
| human15 | 1.79 | 1.6 | 1.12 | 0.75 | 3.7 | 2.09 |
| CMV1 | 3.55 | 7.82 | 7.91 | 3.5 | 14.5 | 3.86 |

TABLE 6

Effects of novel peptides on NKG2A-/NKG2C+ activation through an increase in percentage of CD107+ NK cells.

| Peptide | Trial 1 | Trial 2 | Trial 3 | Trial 4 | Trial 5 | Trial 6 |
|---|---|---|---|---|---|---|
| VMAPQSLLL (PQS) (SEQ ID NO: 17) | 25.2 | 32.8 | 58.6 | 53.6 | 43 | 22.3 |
| VMAPRTLFL (LFL) (SEQ ID NO: 18) | 82.2 | 86.6 | 88.7 | 68.3 | 78.6 | 56.3 |
| VMAPRTLIL (LIL) (SEQ ID NO: 19) | 74.1 | 87 | 85.3 | 73.4 | 79.9 | 63.2 |
| human1 | 74.8 | 87.4 | 87 | 68.2 | 75.8 | 57.6 |
| human2 | 80 | 87.3 | 88.3 | 71.7 | 69.9 | 59.3 |
| human3 | 50.7 | 63.4 | 73.9 | 62.3 | 61 | 39.5 |
| human4 | 76.7 | 79.5 | 84.8 | 73.4 | 77.9 | 64.2 |
| human5 | 59.7 | 61.8 | 72.6 | 64.3 | 67.6 | 46.8 |
| human7 | 76.2 | 89.5 | 87.7 | 63.2 | 76.5 | 55.3 |
| human8 | 73.7 | 82.1 | 84.3 | 64.8 | 70.7 | 53.1 |
| human11 | 70.6 | 79.9 | 81 | 66.8 | 70.2 | 42.5 |
| human12 | 36.5 | 77 | 80.3 | | | |
| human13 | 38.3 | 57 | 71.2 | 57.1 | 56.2 | 29.1 |
| human14 | 61.3 | 83.1 | 85 | 59.1 | 70.5 | 44.3 |
| human15 | 78.4 | 86 | 88.2 | 68.9 | 78 | 56.2 |
| CMV1 | 77.3 | 87.2 | 86.2 | 67.3 | 76.9 | 53.4 |

TABLE 7

Effects of novel peptides on NKG2A-/NKG2C+ activation through an increase in percentage of IFNG+ NK cells.

| Peptide | Trial 1 | Trial 2 | Trial 3 | Trial 4 | Trial 5 | Trial 6 |
|---|---|---|---|---|---|---|
| VMAPQSLLL (PQS) (SEQ ID NO: 17) | 10.6 | 12.7 | 40.7 | 35.6 | 19.9 | 10.3 |
| VMAPRTLFL (LFL) (SEQ ID NO: 18) | 69.3 | 83.7 | 85.3 | 64.7 | 73.5 | 51.9 |
| VMAPRTLIL (LIL) (SEQ ID NO: 19) | 64.1 | 79.8 | 78.1 | 59.7 | 72.5 | 45.9 |
| human1 | 62.6 | 84.1 | 80.5 | 58.1 | 66.9 | 46.7 |
| human2 | 69.5 | 82.3 | 83 | 64.5 | 63.2 | 50.7 |
| human3 | 27.8 | 36.4 | 55.4 | 46.9 | 43.5 | 23.3 |
| human4 | 62.2 | 70.5 | 75.9 | 66.6 | 70.4 | 54 |
| human5 | 35.3 | 43.2 | 57.2 | 51.1 | 53.4 | 28.6 |
| human7 | 66.6 | 87.3 | 79.8 | 54.1 | 70 | 45.4 |
| human8 | 58.6 | 74.8 | 74.5 | 54 | 62.3 | 43.8 |
| human11 | 63.1 | 76.4 | 76.8 | 59.4 | 65 | 35.3 |
| human12 | 20.7 | 63.3 | 66.3 | | | |
| human13 | 18.2 | 28.7 | 49.2 | 40.8 | 34.2 | 14.3 |

TABLE 7-continued

Effects of novel peptides on NKG2A-/NKG2C+ activation through an increase in percentage of IFNG+ NK cells.

| Peptide | Trial 1 | Trial 2 | Trial 3 | Trial 4 | Trial 5 | Trial 6 |
|---|---|---|---|---|---|---|
| human14 | 45.6 | 72.7 | 74.2 | 47.5 | 61.9 | 30.5 |
| human15 | 66.7 | 79.9 | 78.8 | 60.9 | 71.9 | 44.1 |
| CMV1 | 66.3 | 82.8 | 78.5 | 58.2 | 69.5 | 42.5 |

TABLE 8

Effects of novel peptides on NKG2A-/NKG2C+ activation through an increase in percentage of TNF+ NK cells.

| Peptide | Trial 1 | Trial 2 | Trial 3 | Trial 4 | Trial 5 | Trial 6 |
|---|---|---|---|---|---|---|
| VMAPQSLLL (PQS) (SEQ ID NO: 17) | 4.96 | 9.31 | 31.2 | 25.7 | 14.7 | 5.08 |
| VMAPRTLFL (LFL) (SEQ ID NO: 18) | 50.4 | 76.6 | 77 | 53.3 | 64.4 | 28.7 |
| VMAPRTLIL (LIL) (SEQ ID NO: 19) | 48.5 | 62.5 | 61.4 | 50.4 | 66.3 | 35.5 |
| human1 | 51.1 | 75.2 | 72.9 | 51.6 | 64 | 38.8 |
| human2 | 57.3 | 72.6 | 73.8 | 56.2 | 57.8 | 41.1 |
| human3 | 19.1 | 24.8 | 47.1 | 37.4 | 37.7 | 15.8 |
| human4 | 49.6 | 57.3 | 65.5 | 57.4 | 64.7 | 43 |
| human5 | 17.4 | 23.9 | 42.2 | 36 | 40.4 | 15 |
| human7 | 54.5 | 79.9 | 70.1 | 47.8 | 66.1 | 37.8 |
| human8 | 45.1 | 64 | 63.7 | 43.7 | 57.1 | 31.7 |
| human11 | 57.2 | 71.3 | 72 | 53.6 | 62.5 | 33.5 |
| human12 | 12.6 | 52.7 | 59.6 | | | |
| human13 | 9.29 | 20.7 | 37.9 | 33 | 27.4 | 8.92 |
| human14 | 31.9 | 65.1 | 65 | 40 | 57.9 | 21.8 |
| human15 | 52.1 | 71.8 | 68.2 | 52.6 | 66.6 | 36.3 |
| CMV1 | 53.3 | 76.1 | 68.8 | 51 | 66 | 33.3 |

TABLE 9

Effects of novel peptides on NKG2A-/NKG2C+ activation through an increase in percentage of CCL3+ NK cells.

| Peptide | Trial 1 | Trial 2 | Trial 3 | Trial 4 | Trial 5 | Trial 6 |
|---|---|---|---|---|---|---|
| VMAPQSLLL (PQS) (SEQ ID NO: 17) | 47 | 55.3 | 69.4 | 58.6 | 55.4 | 32.7 |
| VMAPRTLFL (LFL) (SEQ ID NO: 18) | 84.1 | 89.2 | 88 | 73.7 | 84.1 | 62.9 |
| VMAPRTLIL (LIL) (SEQ ID NO: 19) | 76.7 | 92 | 85.4 | 69 | 79.6 | 56.6 |
| human1 | 78.3 | 91.5 | 86.6 | 68.1 | 79.1 | 61.1 |

TABLE 9-continued

| Effects of novel peptides on NKG2A-/NKG2C+ activation through an increase in percentage of CCL3+ NK cells. | | | | | | |
|---|---|---|---|---|---|---|
| Peptide | Trial 1 | Trial 2 | Trial 3 | Trial 4 | Trial 5 | Trial 6 |
| human2 | 80.9 | 92.4 | 86.1 | 71.8 | 75.8 | 62.1 |
| human3 | 60.9 | 75.8 | 75.7 | 64.5 | 65.7 | 46 |
| human4 | 77.9 | 87.9 | 84.4 | 74 | 81.2 | 64.6 |
| human5 | 60.9 | 74.5 | 72.5 | 63.8 | 69.7 | 47.2 |
| human7 | 77 | 92.4 | 87.5 | 61.5 | 77.3 | 55.6 |
| human8 | 75.5 | 89 | 84.1 | 65.3 | 74.6 | 57 |
| human11 | 72.1 | 83.5 | 80.8 | 65 | 69.8 | 39.9 |
| human12 | 55.3 | 83.9 | 81.7 | | | |
| human13 | 56.9 | 74.9 | 72.4 | 60.7 | 61.9 | 40.7 |
| human14 | 70.6 | 87.5 | 82.5 | 61.1 | 71.8 | 52.1 |
| human15 | 79.5 | 89.7 | 86.8 | 69 | 78.9 | 58.4 |
| CMV1 | 80.1 | 90.4 | 86.5 | 67.5 | 78.1 | 58.3 |

TABLE 10

| Effects of novel peptides on NKG2A-/NKG2C- controls through percentage CD107+ NK cells. | | | | | | |
|---|---|---|---|---|---|---|
| Peptide | Trial 1 | Trial 2 | Trial 3 | Trial 4 | Trial 5 | Trial 6 |
| VMAPQSLLL (PQS) (SEQ ID NO: 17) | 24.1 | 37.9 | 53 | 28 | 24.4 | 19.5 |
| VMAPRTLFL (LFL) (SEQ ID NO: 18) | 29.2 | 28.2 | 45.1 | 31.4 | 20.1 | 20.9 |
| VMAPRTLIL (LIL) (SEQ ID NO: 19) | 24.4 | 33.4 | 43.2 | 26.4 | 17.9 | 19 |
| human1 | 25.1 | 37.6 | 47.2 | 29.5 | 19.8 | 18.8 |
| human2 | 26.1 | 34.1 | 46.1 | 30.1 | 18.1 | 19.1 |
| human3 | 28.9 | 37.9 | 50.4 | 32.6 | 26.2 | 18.6 |
| human4 | 27.2 | 33.5 | 44 | 32.1 | 19.2 | 22.6 |
| human5 | 26.5 | 32.5 | 48.1 | 27.8 | 19 | 20.1 |
| human7 | 21.8 | 27.4 | 41.8 | 24 | 17.2 | 20.5 |
| human8 | 27.7 | 36.2 | 47.3 | 28.6 | 20.2 | 19.3 |
| human11 | 21.7 | 28.7 | 38.6 | 28.9 | 14.9 | 14.8 |
| human12 | 20.2 | 29 | 42 | | | |
| human13 | 26.3 | 43 | 56.4 | 31.8 | 22.7 | 21.1 |
| human14 | 20.9 | 31.4 | 43.7 | 25.6 | 21.8 | 16.7 |
| human15 | 25.7 | 34.1 | 43.7 | 29.6 | 18.9 | 21.1 |
| CMV1 | 21.4 | 32.5 | 41.9 | 25.7 | 18.6 | 14.5 |

TABLE 11

Effects of novel peptides on NKG2A-/NKG2C- controls through percentage of IFNG+ NK cells.

| Peptide | Trial 1 | Trial 2 | Trial 3 | Trial 4 | Trial 5 | Trial 6 |
|---|---|---|---|---|---|---|
| VMAPQSLLL (PQS) (SEQ ID NO: 17) | 14 | 27.9 | 48.3 | 19 | 18.6 | 10 |
| VMAPRTLFL (LFL) (SEQ ID NO: 18) | 17.6 | 20.1 | 39.2 | 23 | 14.4 | 11.1 |
| VMAPRTLIL (LIL) (SEQ ID NO: 19) | 15.5 | 22.8 | 36.7 | 18.7 | 12.1 | 9.39 |
| human1 | 16.2 | 29.3 | 38.5 | 18.6 | 15.9 | 7.82 |
| human2 | 16.2 | 24.9 | 37.4 | 18.9 | 13.9 | 10 |
| human3 | 17.2 | 26.9 | 44 | 21.2 | 19.1 | 8.37 |
| human4 | 15.4 | 20.8 | 33.7 | 19.3 | 13.7 | 12.1 |
| human5 | 14.6 | 26.3 | 41.4 | 18.7 | 14.6 | 10.7 |
| human7 | 13.3 | 23.4 | 34.9 | 16.4 | 12.7 | 10.9 |
| human8 | 14.7 | 28.8 | 38 | 18.6 | 14.2 | 10.9 |
| human11 | 11.4 | 21.3 | 33.5 | 18.5 | 10.5 | 6.09 |
| human12 | 10.2 | 24 | 36.2 | | | |
| human13 | 16.6 | 32.5 | 49.4 | 22.2 | 18.9 | 8.06 |
| human14 | 12.1 | 27.7 | 36.5 | 17.5 | 16.7 | 7.36 |
| human15 | 15.5 | 25.4 | 34.7 | 20.3 | 14.7 | 11.9 |
| CMV1 | 13.5 | 27.7 | 36.7 | 17.4 | 14.6 | 8.57 |

TABLE 12

Effects of novel peptides on NKG2A-/NKG2C- controls through percentage TNF+ NK cells.

| Peptide | Trial 1 | Trial 2 | Trial 3 | Trial 4 | Trial 5 | Trial 6 |
|---|---|---|---|---|---|---|
| VMAPQSLLL (PQS) (SEQ ID NO: 17) | 3.46 | 9.07 | 22.6 | 8.23 | 8.67 | 4.08 |
| VMAPRTLFL (LFL) (SEQ ID NO: 18) | 3.45 | 6.56 | 17 | 9.55 | 5.27 | 4.76 |
| VMAPRTLIL (LIL) (SEQ ID NO: 19) | 3.46 | 7.41 | 13.6 | 8.21 | 4.32 | 3.8 |
| human1 | 4.84 | 11.3 | 19 | 9.26 | 6.91 | 3.78 |
| human2 | 4.12 | 8.51 | 15.8 | 9.02 | 6.52 | 5.25 |
| human3 | 4.31 | 8.81 | 20.8 | 11.3 | 8.06 | 4.18 |
| human4 | 3.99 | 7.5 | 13.8 | 10.2 | 5.02 | 5.37 |
| human5 | 4.11 | 10.4 | 18 | 9.09 | 6.08 | 4.34 |
| human7 | 4.13 | 7.88 | 14.2 | 7.92 | 5.21 | 4.34 |
| human8 | 4.82 | 10.5 | 16.5 | 9.61 | 6.07 | 3.78 |
| human11 | 3.75 | 7.72 | 14.8 | 9.48 | 3.82 | 2.69 |
| human12 | 3.43 | 9.58 | 15.5 | | | |
| human13 | 3.65 | 11.9 | 23.2 | 12.1 | 8.01 | 3.64 |

TABLE 12-continued

| Effects of novel peptides on NKG2A-/NKG2C- controls through percentage TNF+ NK cells. | | | | | | |
|---|---|---|---|---|---|---|
| Peptide | Trial 1 | Trial 2 | Trial 3 | Trial 4 | Trial 5 | Trial 6 |
| human14 | 2.61 | 9.25 | 17.1 | 8.96 | 7.19 | 2.97 |
| human15 | 3.42 | 9.68 | 14.8 | 10.3 | 6.97 | 5.43 |
| CMV1 | 2.62 | 9.43 | 13.6 | 8.63 | 6.68 | 2.86 |

TABLE 13

| Effects of novel peptides on NKG2A-/NKG2C- controls through percentage CCL3+ NK cells. | | | | | | |
|---|---|---|---|---|---|---|
| Peptide | Trial 1 | Trial 2 | Trial 3 | Trial 4 | Trial 5 | Trial 6 |
| VMAPQSLLL (PQS) (SEQ ID NO: 17) | 35.1 | 57.7 | 59.4 | 35 | 34 | 22.4 |
| VMAPRTLFL (LFL) (SEQ ID NO: 18) | 39.4 | 43.3 | 47.7 | 35.9 | 26.5 | 23.2 |
| VMAPRTLIL (LIL) (SEQ ID NO: 19) | 31.4 | 54 | 46.1 | 30.8 | 23.8 | 21.4 |
| human1 | 37 | 59.6 | 51.3 | 33.1 | 26 | 24.1 |
| human2 | 31.9 | 57.4 | 49.9 | 34.8 | 25.6 | 24.6 |
| human3 | 38.1 | 61 | 55.4 | 36.6 | 31 | 26.5 |
| human4 | 37.2 | 56.3 | 48.3 | 35.9 | 25 | 25.1 |
| human5 | 33 | 55.5 | 53.4 | 30.6 | 23.5 | 22 |
| human7 | 30.7 | 49.5 | 47 | 27.4 | 22.9 | 22.6 |
| human8 | 33.5 | 60.3 | 52.4 | 32 | 29.2 | 24.8 |
| human11 | 27.1 | 49.5 | 44.1 | 30.9 | 18.3 | 13.7 |
| human12 | 29.3 | 51.6 | 46.5 | | | |
| human13 | 37.2 | 65.4 | 56.2 | 37.7 | 30.1 | 27.4 |
| human14 | 29.3 | 54.7 | 44 | 29.2 | 26.9 | 20.9 |
| human15 | 34 | 55.5 | 46.7 | 34.3 | 24.7 | 26.4 |
| CMV1 | 29.9 | 52.4 | 47.3 | 27.2 | 26.6 | 19.1 |

Example 2: Determining Peptide Relative Granularity of Activating Response in an Antigen-Processing-Defective Cell Line An antigen processing-defective lymphoma cell line (RMA-S), with a low-level expression of HLA-E, were incubated with the novel peptides to determine the inhibitory strength on NKG2A−/NKG2C+NK cells relative to positive control sequences with differential effects (VMAPRTLIL (SEQ ID NO: 19)/VMAPRTLFL (SEQ ID NO: 18)). The effects of the peptides on NK cell inhibition were determined by measuring four markers of NK cell activation (CD107a, IFNG, TNF, CCL3) in NKG2A−/NKG2C+NK cells (FIGS. 2A-2D). Activation was indicated by an increase in percent cells positive for cell surface markers.

The three peptides (h3, h5, h13) which resulted in selective NK cell activation in Example 1, caused differential levels of activation following exposure in RMA-S lymphoma cells. Peptide h5 showed the strongest NK cell activation, comparable with the positive control peptides for several markers assessed (FIGS. 2A-2D). Peptides h3 and h13 showed slight increases in CD107a (FIG. 2A) and CCL3 (FIG. 2D), but no increase in TNF (FIG. 2B) and IFNG (FIG. 2C) cell surface markers relative to positive control peptides.

Peptides that previously demonstrated to have mild inhibitory effects (h1, h2, h4, h8) and strong activating effects in Example 1, showed similar effects on NKG2A−/NKG2C+NK cell activation relative to controls following peptide exposures in RMA-S lymphoma cells (FIGS. 2A-2D). Peptides h7, h11, h15, and CMV1 elicited activation of NKG2A−/NKG2C+NK cells (FIGS. 2A-2D) similar to the positive control peptides. Interestingly, peptide h14 resulted in decreased NK cell activation relative to the positive control peptides.

Figure 3:
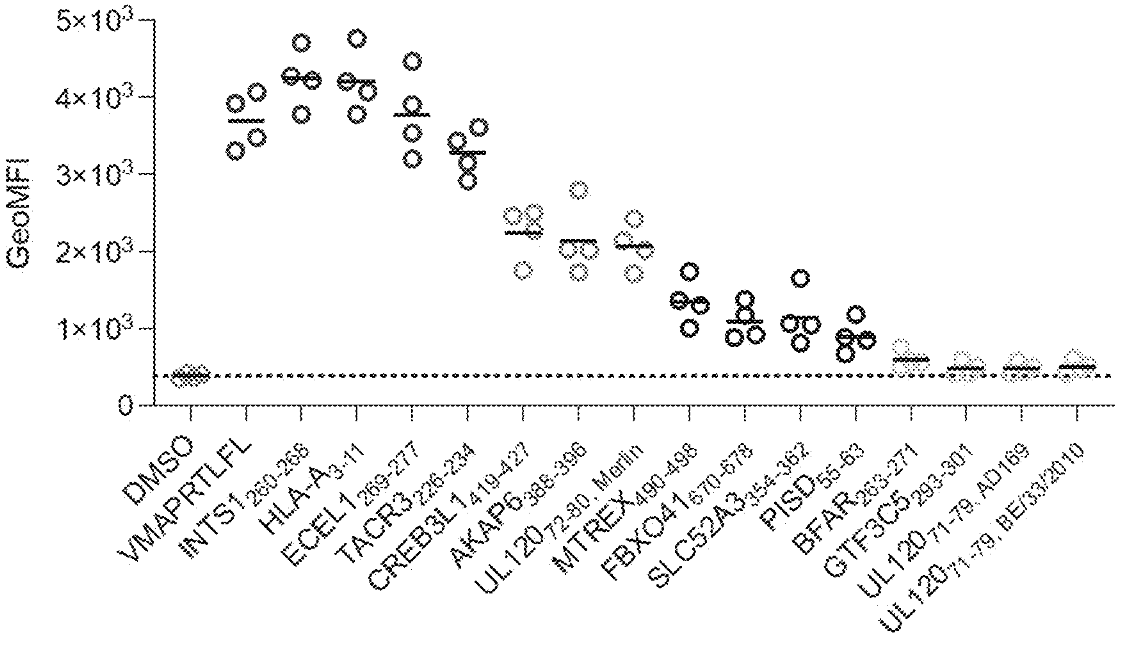
FIG. 3 shows the assessment of peptide-HLA-E binding via a HLA-E surface stabilization assay with RMA-S/HLA-E cells incubated with 30 μM of a peptide. HLA-E expression is detected with an anti-HLA-E antibody. Measurements from replicate experiments are shown, with solid black lines indicating mean values.
Figure 4A:
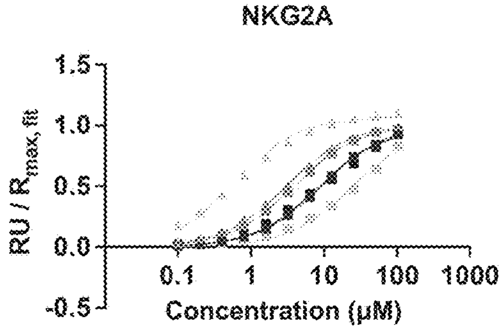
FIGS. 4A-4D shows surface plasmon resonance of proteome-derived peptides with CD94/NKG2A and CD94/NKG2C.
Figure 4B:
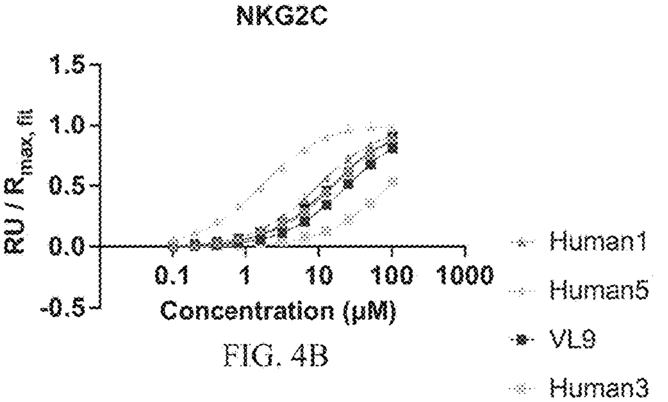
Figure 4C:
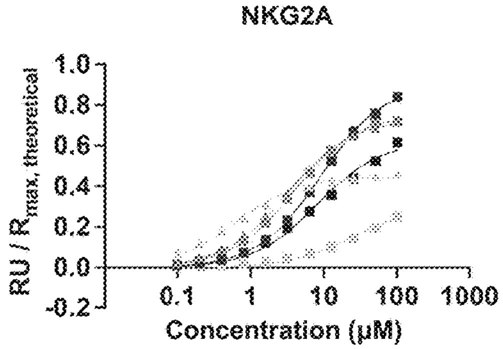
Figure 4D:
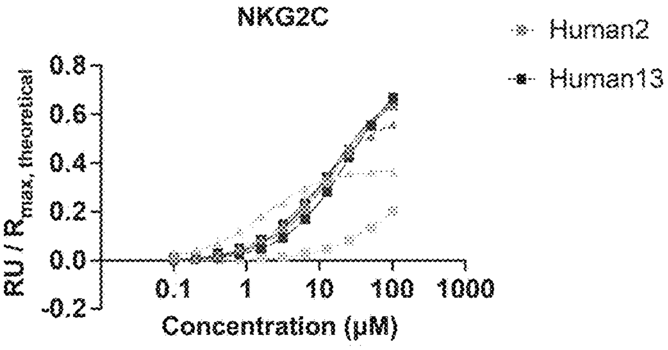

Example 3: Determining HLA-E Surface Expression Stabilization and Binding Affinity of Proteome-Derived Peptides to CD94/NKG2A or CD94/NKG2C An antigen processing-defective lymphoma cell line (RMA-S), with a low-level expression of HLA-E, were incubated with 30 μM of each individual novel peptide for 16 hours to determine HLA-E surface expression stabilization strength relative to a positive control sequence (VMAPRTLFL (SEQ ID NO: 18)). HLA-E surface expression was assessed by measuring geometric mean fluorescence intensity (GeoMFI) in RMA-S cells following immunofluorescence staining with an anti-HLA-E antibody (Table 14). Increased GeoMFI was indicative of increased HLA-E surface expression stability following novel peptide exposures (FIG. 3). Peptides with the highest HLA-E surface expression stabilization strength, i.e., approximately $3\times10^3$ to $4\times10^3$ GeoMFI, included VMAPRTLFL (SEQ ID NO: 18), $INTS1_{260-268}$, $HLA\text{-}A_{3-11}$, $ECEL_{269-277}$, and $TACR3_{226-234}$. Peptides with moderate HLA-E surface expression stabilization strength, i.e., approximately $2\times10^3$ GeoMFI, included $CREB3L1_{419-427}$, $AKAP6_{388-396}$, and $UL120_{72-80,\ Merlin}$. Peptides with lower HLA-E surface expression stabilization strength, i.e., approximately $1\times10^3$ GeoMFI, included $MTREX_{490-498}$, $FBXO41_{670-678}$, $SLC52A3_{354-362}$, and $PISD_{55-63}$. Peptides with the lowest HLA-E surface expression stabilization strength, i.e., closest to the experimental negative control (DMSO), included $BFAR_{263-271}$, $GTF3C5_{293-301}$, $UL120_{71-79,\ AD169}$, and $UL120_{71-79,\ BE/33/2010}$.

TABLE 14

HLA-E surface expression stability (GeoMFI) following exposure to novel peptides.

| Peptide | Trial 1 | Trial 2 | Trial 3 | Trial 4 |
|---|---|---|---|---|
| DMSO | 411 | 354 | 363 | 424 |
| VMAPRTLFL (LFL) (SEQ ID NO: 18) | 3477 | 3307 | 3920 | 4064 |
| $CREB3L1_{419-427}$ (human1) | 2461 | 1755 | 2273 | 2496 |
| $AKAP6_{388-396}$ (human2) | 2019 | 2029 | 1731 | 2795 |
| $GTF3C5_{293-301}$ (human3) | 510 | 428 | 421 | 596 |
| $FBXO41_{670-678}$ (human4) | 1174 | 921 | 887 | 1378 |
| $BFAR_{263-271}$ (human5) | 569 | 509 | 566 | 750 |
| $ECEL1_{269-277}$ (human7) | 3203 | 3535 | 3903 | 4464 |
| $SLC52A3_{354-362}$ (human8) | 1066 | 813 | 1049 | 1654 |
| $TACR3_{226-234}$ (human11) | 3152 | 2914 | 3432 | 3610 |
| $INTS1_{260-268}$ (human12) | 3779 | 4219 | 4273 | 4705 |
| $PISD_{55-63}$ (human13) | 851 | 887 | 673 | 1187 |
| $MTREX_{490-498}$ (human13) | 1304 | 1364 | 1005 | 1738 |
| $HLA\text{-}A_{3-11}$ (human15) | 3783 | 4068 | 4205 | 4760 |
| UL $120_{72-80,Merlin}$ (CMV1) | 2140 | 1714 | 2014 | 2421 |

Binding affinity of novel peptides linked to HLA-E was determined using surface plasmon resonance (SPR), a methodology used to study protein-protein interactions (Tables 15-19). The peptide-HLA-E complex (generated as a single chain trimer) was immobilized on the sensor chip surface and CD94/NKG2A or CD94/NKG2C were flowed over. Steady-state surface plasmon resonance experiments were performed with a Biacore T200 instrument. CD94/NKG2x in HBS-EP+ buffer was injected as analyte in a concentration range of 0.1 μM to 102.4 μM and flow rate of 10 μL/min at 25° C. Data was fit with Prism 9.4 (GraphPad Software Inc; San Diego CA) to a "one site, specific binding" model. Series S CM5 chips were coupled to neutravidin and utilized. Biotinylated pMHC was immobilized at approximately 400 RU. $K_D$ values calculated by Biacore software are reported. Rmax, fit values were calculated by Biacore software. Rmax, theoretical values were calculated using the analyte/ligand mass ratio (0.66) multiplied by the amount of ligand coupled to the chip.

The binding affinities of novel proteins with varying HLA-E surface expression stabilization strength including VMAPRTLFL (SEQ ID NO: 18) (higher), $CREB3L1_{419-427}$ (moderate), $AKAP6_{388-396}$ (moderate), $PISD_{55-63}$ (lower), $BFAR_{263-271}$ (lowest), and $GTF3C5_{293-301}$ (lowest) were tested (FIGS. 4A-4D). HLA-E-peptides comprising the VMAPRTLFL (SEQ ID NO: 18) control resulted in $K_D$ values of 8.9 and 23.8 for CD94/NKG2A and CD94/NKG2C, respectively. Surprisingly, novel peptides with weaker HLA-E surface expression strength had increased CD94/NKG2A and CD94/NKG2C affinity (Table 14 and Table 19) similar to peptides with stronger HLA-E stability. Based on the above stabilization and SPR data, it appears that one hallmark of selective activators is they have lower affinity for HLA-E, while peptide-HLA-E complexes retain affinity for CD94/NKG2A and CD94/NKG2C.

TABLE 15

Binding affinities of peptide-HLA-E complexes to CD94/NKG2A normalized to a fitted $R_{max}$.

| Concentration (μM) | Human1 | Human5 | VL9 | Human3 | Human2 | Human13 |
|---|---|---|---|---|---|---|
| 0 | −0.006 | −0.002 | −0.003 | 0.013 | −0.007 | 0.010 |
| 0.1 | 0.035 | 0.177 | 0.011 | 0.015 | 0.023 | 0.024 |
| 0.2 | 0.068 | 0.288 | 0.021 | 0.019 | 0.046 | 0.037 |
| 0.4 | 0.128 | 0.434 | 0.044 | 0.030 | 0.094 | 0.066 |
| 0.8 | 0.221 | 0.593 | 0.082 | 0.051 | 0.173 | 0.115 |
| 1.6 | 0.349 | 0.739 | 0.150 | 0.086 | 0.293 | 0.191 |
| 3.2 | 0.506 | 0.863 | 0.260 | 0.145 | 0.450 | 0.302 |
| 6.4 | 0.664 | 0.955 | 0.408 | 0.231 | 0.618 | 0.432 |
| 12.8 | 0.798 | 1.018 | 0.579 | 0.336 | 0.766 | 0.558 |
| 25.6 | 0.896 | 1.059 | 0.741 | 0.472 | 0.873 | 0.685 |
| 51.2 | 0.950 | 1.081 | 0.837 | 0.639 | 0.942 | 0.819 |
| 102.4 | 0.996 | 1.105 | 0.926 | 0.827 | 0.954 | 0.961 |

TABLE 16

Binding affinities of peptide-HLA-E compliexes to CD94/NKG2C normalized to a fitted $R_{max}$.

| Concentration (μM) | Human1 | Human5 | VL9 | Human3 | Human2 | Human13 |
|---|---|---|---|---|---|---|
| 0 | −0.007 | −0.001 | −0.003 | 0.006 | −0.005 | 0.007 |
| 0.1 | 0.007 | 0.064 | 0.003 | 0.008 | 0.003 | 0.017 |
| 0.2 | 0.017 | 0.119 | 0.006 | 0.007 | 0.009 | 0.023 |
| 0.4 | 0.038 | 0.205 | 0.014 | 0.011 | 0.023 | 0.040 |
| 0.8 | 0.076 | 0.333 | 0.031 | 0.016 | 0.046 | 0.067 |
| 1.6 | 0.144 | 0.488 | 0.061 | 0.026 | 0.089 | 0.117 |
| 3.2 | 0.246 | 0.650 | 0.114 | 0.044 | 0.168 | 0.202 |
| 6.4 | 0.394 | 0.795 | 0.208 | 0.078 | 0.281 | 0.317 |
| 12.8 | 0.564 | 0.902 | 0.344 | 0.130 | 0.443 | 0.462 |
| 25.6 | 0.723 | 0.971 | 0.517 | 0.219 | 0.621 | 0.613 |
| 51.2 | 0.832 | 0.990 | 0.677 | 0.353 | 0.755 | 0.746 |
| 102.4 | 0.912 | 0.983 | 0.810 | 0.537 | 0.867 | 0.904 |

TABLE 17

Binding affinities of peptide-HLA-E compliexes to CD94/NKG2A normalized to a theoretical $R_{max}$.

| Concentration (μM) | Human1 | Human5 | VL9 | Human3 | Human2 | Human13 |
|---|---|---|---|---|---|---|
| 0.000 | −0.005 | −0.001 | −0.003 | 0.004 | −0.005 | 0.006 |
| 0.100 | 0.025 | 0.074 | 0.010 | 0.005 | 0.017 | 0.015 |
| 0.200 | 0.049 | 0.120 | 0.019 | 0.006 | 0.034 | 0.023 |
| 0.400 | 0.093 | 0.181 | 0.040 | 0.009 | 0.070 | 0.042 |

TABLE 17-continued

Binding affinities of peptide-HLA-E compliexes to CD94/NKG2A normalized to a theoretical $R_{max}$.

| Concentration (μM) | Human1 | Human5 | VL9 | Human3 | Human2 | Human13 |
|---|---|---|---|---|---|---|
| 0.800 | 0.160 | 0.247 | 0.075 | 0.015 | 0.131 | 0.074 |
| 1.600 | 0.252 | 0.308 | 0.136 | 0.026 | 0.221 | 0.122 |
| 3.200 | 0.365 | 0.360 | 0.236 | 0.044 | 0.339 | 0.193 |
| 6.400 | 0.479 | 0.398 | 0.370 | 0.070 | 0.465 | 0.277 |
| 12.800 | 0.577 | 0.425 | 0.525 | 0.102 | 0.577 | 0.357 |
| 25.600 | 0.647 | 0.442 | 0.671 | 0.143 | 0.657 | 0.439 |
| 51.200 | 0.686 | 0.451 | 0.759 | 0.194 | 0.709 | 0.524 |
| 102.400 | 0.719 | 0.461 | 0.839 | 0.250 | 0.718 | 0.615 |

TABLE 18

Binding affinities of peptide-HLA-E compliexes to CD94/NKG2C normalized to a theoretical $R_{max}$.

| Concentration (μM) | Human1 | Human5 | VL9 | Human3 | Human2 | Human13 |
|---|---|---|---|---|---|---|
| 0 | −0.004 | 0.000 | −0.003 | 0.002 | −0.003 | 0.005 |
| 0.1 | 0.004 | 0.024 | 0.002 | 0.003 | 0.002 | 0.012 |
| 0.2 | 0.010 | 0.044 | 0.005 | 0.003 | 0.007 | 0.017 |
| 0.4 | 0.023 | 0.076 | 0.012 | 0.004 | 0.017 | 0.030 |
| 0.8 | 0.047 | 0.123 | 0.025 | 0.006 | 0.034 | 0.050 |
| 1.6 | 0.088 | 0.180 | 0.050 | 0.010 | 0.066 | 0.086 |
| 3.2 | 0.151 | 0.240 | 0.094 | 0.017 | 0.124 | 0.149 |
| 6.4 | 0.242 | 0.294 | 0.171 | 0.030 | 0.207 | 0.234 |
| 12.8 | 0.346 | 0.333 | 0.282 | 0.050 | 0.326 | 0.342 |
| 25.6 | 0.444 | 0.359 | 0.425 | 0.084 | 0.457 | 0.454 |
| 51.2 | 0.511 | 0.366 | 0.556 | 0.135 | 0.555 | 0.552 |
| 102.4 | 0.560 | 0.363 | 0.665 | 0.205 | 0.638 | 0.669 |

TABLE 19

Affinities of novel peptides in a HLA-peptide complex to receptors.

| | NKG2A (μM affinity) | NKG2C (μM affinity) |
|---|---|---|
| VMAPRTLFL (SEQ ID NO: 18) | 8.9 | 23.8 |
| $CREB3L1_{419-427}$ | 3.3 | 9.8 |
| $AKAP6_{388-396}$ | 4.1 | 15.6 |
| $PISD_{55-63}$ | 12.1 | 16.0 |
| $BFAR_{263-271}$ | 0.8 | 1.8 |
| $GTF3C5_{293-301}$ | 28.1* | 92.4* |

SEQUENCE LISTING

```
Sequence total quantity: 19
SEQ ID NO: 1            moltype = AA  length = 9
FEATURE                 Location/Qualifiers
source                  1..9
                        mol_type = protein
                        organism = Synthetic construct
SEQUENCE: 1
XXPXRSLXX                                                         9

SEQ ID NO: 2            moltype = AA  length = 9
FEATURE                 Location/Qualifiers
source                  1..9
                        mol_type = protein
                        organism = Synthetic construct
SEQUENCE: 2
TGPWRSLWI                                                         9

SEQ ID NO: 3            moltype = AA  length = 9
FEATURE                 Location/Qualifiers
source                  1..9
                        mol_type = protein
```

```
                        organism = Synthetic construct
SEQUENCE: 3
VNPGRSLFL                                                        9

SEQ ID NO: 4            moltype = AA  length = 9
FEATURE                 Location/Qualifiers
source                  1..9
                        mol_type = protein
                        organism = Synthetic construct
SEQUENCE: 4
XXPXRXXFL                                                        9

SEQ ID NO: 5            moltype = AA  length = 9
FEATURE                 Location/Qualifiers
source                  1..9
                        mol_type = protein
                        organism = Synthetic construct
SEQUENCE: 5
TAPARTMFL                                                        9

SEQ ID NO: 6            moltype = AA  length = 9
FEATURE                 Location/Qualifiers
source                  1..9
                        mol_type = protein
                        organism = Synthetic construct
SEQUENCE: 6
NMPARTVLF                                                        9

SEQ ID NO: 7            moltype = AA  length = 9
FEATURE                 Location/Qualifiers
source                  1..9
                        mol_type = protein
                        organism = Synthetic construct
SEQUENCE: 7
QMPSRSLLF                                                        9

SEQ ID NO: 8            moltype = AA  length = 9
FEATURE                 Location/Qualifiers
source                  1..9
                        mol_type = protein
                        organism = Synthetic construct
SEQUENCE: 8
TLPKRGLFL                                                        9

SEQ ID NO: 9            moltype = AA  length = 9
FEATURE                 Location/Qualifiers
source                  1..9
                        mol_type = protein
                        organism = Synthetic construct
SEQUENCE: 9
ILTDRSLWL                                                        9

SEQ ID NO: 10           moltype = AA  length = 9
FEATURE                 Location/Qualifiers
source                  1..9
                        mol_type = protein
                        organism = Synthetic construct
SEQUENCE: 10
FLPNRSLLF                                                        9

SEQ ID NO: 11           moltype = AA  length = 9
FEATURE                 Location/Qualifiers
source                  1..9
                        mol_type = protein
                        organism = Synthetic construct
SEQUENCE: 11
TLPERTLYL                                                        9

SEQ ID NO: 12           moltype = AA  length = 9
FEATURE                 Location/Qualifiers
source                  1..9
                        mol_type = protein
                        organism = Synthetic construct
SEQUENCE: 12
VMPGRTLCF                                                        9

SEQ ID NO: 13           moltype = AA  length = 9
FEATURE                 Location/Qualifiers
source                  1..9
```

-continued

```
                        mol_type = protein
                        organism = Synthetic construct
SEQUENCE: 13
RMPPRSVLL                                                        9

SEQ ID NO: 14           moltype = AA  length = 9
FEATURE                 Location/Qualifiers
source                  1..9
                        mol_type = protein
                        organism = Synthetic construct
SEQUENCE: 14
VMPPRTLLL                                                        9

SEQ ID NO: 15           moltype = AA  length = 9
FEATURE                 Location/Qualifiers
source                  1..9
                        mol_type = protein
                        organism = Synthetic construct
SEQUENCE: 15
VLPHRTQFL                                                        9

SEQ ID NO: 16           moltype = AA  length = 9
FEATURE                 Location/Qualifiers
source                  1..9
                        mol_type = protein
                        organism = Synthetic construct
SEQUENCE: 16
VMAPRTLXL                                                        9

SEQ ID NO: 17           moltype = AA  length = 9
FEATURE                 Location/Qualifiers
source                  1..9
                        mol_type = protein
                        organism = Synthetic construct
SEQUENCE: 17
VMAPQSLLL                                                        9

SEQ ID NO: 18           moltype = AA  length = 9
FEATURE                 Location/Qualifiers
source                  1..9
                        mol_type = protein
                        organism = Synthetic construct
SEQUENCE: 18
VMAPRTLFL                                                        9

SEQ ID NO: 19           moltype = AA  length = 9
FEATURE                 Location/Qualifiers
source                  1..9
                        mol_type = protein
                        organism = Synthetic construct
SEQUENCE: 19
VMAPRTLIL                                                        9
```

What is claimed is:

1. A peptide comprising $X_1X_2PX_3RSLX_4X_5$ (SEQ ID NO. 1), wherein each X is an amino acid, wherein P is proline, R is Arginine, S is serine, L is Leucine, $X_1$ is Threonine or Valine, $X_2$ is Glycine or Asparagine, $X_3$ is Tryptophan or Glycine, $X_4$ is Tryptophan or Phenylalanine, and $X_5$ is Leucine or Isoleucine, and wherein the peptide is formulated in a nanoparticle and is 9 amino acids in length.

2. The peptide of claim 1, wherein the peptide comprises or consists essentially of TGPWRSLWI (SEQ ID NO. 2).

3. The peptide of claim 1, wherein the peptide comprises or consists essentially of VNPGRSLFL (SEQ ID NO. 3).

4. A peptide comprising $X_1X_6PX_7RX_8X_9FL$ (SEQ ID NO:4), wherein each X is an amino acid, wherein P is proline, R is Arginine, F is Phenylalanine, L is Leucine, $X_1$ is Threonine or Valine, $X_6$ is Alanine or Asparagine, $X_7$ is Alanine or Glycine, $X_8$ is Serine or Threonine, and $X_9$ is Leucine or Methionine, and wherein the peptide is 9 amino acids in length and is linked to another molecule.

5. The peptide of claim 4, wherein the peptide comprises or consists essentially of TAPARTMFL (SEQ ID NO. 5).

6. The peptide of claim 4, wherein the peptide comprises or consists essentially of VNPGRSLFL (SEQ ID NO. 3).

7. The peptide of claim 1, wherein the peptide is linear.

8. The peptide of claim 1, wherein the peptide is PEGylated.

9. A composition comprising a HLA-E binding peptide, wherein the peptide comprises a sequence selected from TAPARTMFL (SEQ ID NO. 5), VNPGRSLFL (SEQ ID NO. 3), TGPWRSLWI (SEQ ID NO. 2), NMPARTVLF (SEQ ID NO. 6), QMPSRSLLF (SEQ ID NO. 7), TLPKRGLFL (SEQ ID NO. 8), ILTDRSLWL (SEQ ID NO. 9), FLPNRSLLF (SEQ ID NO. 10), TLPERTLYL (SEQ ID NO. 11), VMPGRTLCF (SEQ ID NO. 12), RMPPRSVLL (SEQ ID NO. 13), VMPPRTLLL (SEQ ID NO. 14), VLPHRTQFL (SEQ ID NO. 15), and wherein the peptide is 9 amino acids in length, and a pharmaceutically acceptable carrier that is a nanoparticle.

10. A method for treating a disease in a subject comprising administering to the subject a HLA-E binding peptide, wherein the peptide comprises a NKG2C+ cell activating peptide, wherein the NKG2C+ cell activating peptide comprises a sequence selected from TAPARTMFL (SEQ ID NO. 5), VNPGRSLFL (SEQ ID NO. 3), TGPWRSLWI (SEQ ID NO. 2), QMPSRSLLF (SEQ ID NO. 7), TLPKRGLFL (SEQ ID NO. 8), ILTDRSLWL (SEQ ID NO. 9), and FLPNRSLLF (SEQ ID NO. 10).

11. The method of claim 10, wherein the disease is an infection.

12. The method of claim 11, wherein the infection is *Borrelia burgdorferi*, hepatitis virus, herpes virus, cytomegalovirus (CMV), Epstein bar virus (EBV), or human immunodeficiency virus (HIV).

13. The method of claim 10, wherein the disease is a cancer.

14. A method for treating a disease in a subject comprising administering to the subject a HLA-E binding peptide, wherein the-peptide comprises NKG2A+ cell inhibitory peptide, wherein the NKG2A+ cell inhibitory peptide comprises NMPARTVLF (SEQ ID NO. 6).

15. The method of claim 14, wherein the disease is an autoimmune disease.

16. The method of claim 15, wherein the autoimmune disease is multiple sclerosis, systemic lupus erythematosus, inflammatory bowel disease, rheumatoid arthritis, Graves' disease, autoimmune thyroiditis, autoimmune myositis, discoid lupus erythematosus, Crohns disease, Sjogren's syndrome, Reiter's syndrome, Rheumatoid arthritis, myasthenia gravis, Kawasaki's disease, Celiac disease, Goodpasture's syndrome, or aplastic anemia.

* * * * *